US007785871B2

(12) United States Patent
Reed

(10) Patent No.: US 7,785,871 B2
(45) Date of Patent: Aug. 31, 2010

(54) DNA CLONING VECTOR PLASMIDS AND METHODS FOR THEIR USE

(75) Inventor: Thomas D. Reed, Cincinnati, OH (US)

(73) Assignee: Intrexon Corporation, Blacksburg, VA (US)

(*) Notice: Subject to any disclaimer, the term of this patent is extended or adjusted under 35 U.S.C. 154(b) by 1112 days.

(21) Appl. No.: 10/682,764

(22) Filed: Oct. 9, 2003

(65) Prior Publication Data

US 2004/0185556 A1 Sep. 23, 2004

Related U.S. Application Data

(60) Provisional application No. 60/417,282, filed on Oct. 9, 2002.

(51) Int. Cl.
*C12N 15/00* (2006.01)
*C07H 21/04* (2006.01)

(52) U.S. Cl. .................................. 435/320.1; 536/23.1

(58) Field of Classification Search ........................ None
See application file for complete search history.

(56) References Cited

U.S. PATENT DOCUMENTS

| 4,820,642 | A | 4/1989 | Edman et al. |
|---|---|---|---|
| 5,061,628 | A | 10/1991 | Roberts et al. |
| 5,192,676 | A | 3/1993 | Morgan et al. |
| 5,736,135 | A | 4/1998 | Goeddel et al. |
| 5,919,667 | A | 7/1999 | Gage et al. |
| 6,096,523 | A | 8/2000 | Parrott et al. |
| 6,245,545 | B1 | 6/2001 | Kong et al. |
| 6,248,569 | B1 | 6/2001 | Dunn et al. |
| 5,787,104 | A1 | 2/2003 | Zhu et al. |
| 6,514,737 | B1 | 2/2003 | Zhu et al. |
| 6,562,624 | B2 | 5/2003 | Adach et al. |
| 2002/0146733 | A1 | 10/2002 | Sykes et al. |
| 2003/0188345 | A1* | 10/2003 | Heim et al. .............. 800/294 |
| 2004/0253732 | A1 | 12/2004 | Lapiz-Gauthey et al. |
| 2005/0176099 | A1 | 8/2005 | Saha et al. |
| 2008/0050808 | A1 | 2/2008 | Reed et al. |
| 2008/0085553 | A1 | 4/2008 | Reed et al. |
| 2008/0241915 | A1 | 10/2008 | Reed et al. |
| 2009/0123973 | A1 | 5/2009 | Reed |
| 2009/0170727 | A1 | 7/2009 | Reed |
| 2009/0226976 | A1 | 9/2009 | Reed |

FOREIGN PATENT DOCUMENTS

| GB | 2 393 441 A | 3/2004 |
|---|---|---|
| WO | WO 01/07633 A1 | 2/2001 |

OTHER PUBLICATIONS

Goderis, Inge J.W.M., et al. "A Set of Modular Plant Transformation Vectors Allowing Flexible Insertion of Up to Six Expression Units", Plant Molecular Biology, Sep. 2002, pp. 17-27, XP002412980, ISSN: 0167-4412, vol. 50, No. 1, Kluwer Academic Publishers, Netherlands.

Thomson, J. Michael, et al. "Artificial Gene-Clusters Engineered into Plants Using a Vector System Based on Intron- and Intein-Encoded Endonucleases", In Vitro Cellular & Development Biology, Nov. 2002, pp. 537-542, XP001149513, ISSN: 1054-5476, vol. 38, No. 6, Society for In Vitro Biology, Gaithersburg, MD, US.

Asselbergs, Fred A.M. and Rival, Sylvie "Creation of a Novel, Versatile Multiple Cloning Site Cut by Four Rare-Cutting Homing Endonucleases", Biotechniques, Apr. 1996, pp. 558-562, XP002925648, ISSN: 0736-6205, vol. 20, Informa Life Sciences Publishing, Westborough, MA, US.

Lin, Li, et al. "Efficient Linking and Transfer of Multiple Genes by a Multigene Assembly and Transformation Vector System", Proceedings of the National Academy of Sciences of, U.S.A., May 13, 2003, pp. 5962-5967, XP002323544, ISSN: 0027-8424, vol. 100, No. 10, National Academy of Science, Washington, DC, US.

European Search Report Dated Jan. 22, 2007.

Jayaraj et al., "GeMS: an advanced software package for designing synthetic genes," *Nucleic Acids Research* 33: 3011-3016, Oxford University Press, doi: 10.1093/nar/gki614 (May 23, 2005).

La Fontaine et al., "Eukaryotic Expression Vectors That Replicate to Low Copy Number in Bacteria: Transient Expression of the Menkes Protein," *Plasmid* 39: 245-251, Academic Press (1998).

Lu et al., "Vector NTI, a balanced all-in-one sequence analysis suite," *Briefings in Bioinformatics* 5: 378-388, Henry Stewart Publications (Dec. 2004).

Office Action mailed Oct. 30, 2008 in U.S. Appl. No. 11/233,246, inventor Thomas D. Reed, filed Sep. 22, 2005.

U.S. Appl. No. 11/569,335, inventor Reed, T., filed May 18, 2005.

U.S. Appl. No. 11/840,297 inventor Reed, T., filed Aug. 17, 2007.

U.S. Appl. No. 11/841,380, inventor Reed, T, filed Aug. 20, 2007.

Bray et al., "Physical linkage of the genes for platelet membrane glycoproteins IIb and IIIa," *Proc. Natl. Acad. Sci. U.S.A.* 85: 8683-8687, National Academy Of Sciences (1988).

Zabarovska, V. et al.,"*NotI* passporting to identify species composition of complex microbial systems," *Nucleic Acids Research* 31(2): e5, pp. 1-10,*DOI: 10.1093/nar/gng005*, Oxford University Press (2003).

Office Action mailed May 22, 2009 in U.S. Appl. No. 11/569,335, inventor Thomas D. Reed, filed Feb. 22, 2007.

Office Action mailed Jul. 10, 2009 in U.S. Appl. No. 11/233,246, Reed, T., filed Sep. 22, 2005.

Two pages from the New England BioLabs Online Catalog, http://web.archive.org/web/20020408135531/www.neb.com/neb/frame_cat.html, printed on Jun. 22, 2009.

* cited by examiner

*Primary Examiner*—Nancy Vogel
(74) *Attorney, Agent, or Firm*—Sterne, Kessler, Goldstein & Fox P.L.L.C.

(57) ABSTRACT

The present invention is a group of cloning vector plasmids for use in constructing DNA molecules, such as transgenes, for the purpose of gene expression or analysis of gene expression. The present invention is also a method for using the cloning vector plasmids in a variable series of cloning steps to produce a final transgene product. The plasmid cloning vectors are engineered to minimize the amount of manipulation of DNA fragment components by the end user of the vectors and the methods for their use. Transgenes produced using the invention may be used in a single organism, or in a variety of organisms including bacteria, yeast, mice, and other eukaryotes with little or no further modification.

12 Claims, 11 Drawing Sheets

EcoRI (107)
BamHI (95)
XbaI (83)
HindIII (122)
ApaI (73)
PstI (141)
PspOMI (69)
SphI (153)
EcoRV (56)
PvuII (166)
NgoMIV (47)
PacI (174)
SgrAI (47)
AscI (179)
AsiSI (42)
MluI (186)
PvuI (42)
AflIII (186)
EcoO109I (32)
BspEI (192)
T7 Primer
T3 Primer
BlpI (4)
PmeI (223)

TWV-SVP (MCS-1 F)
234 bp

DNA CLONING VECTOR PLASMIDS AND METHODS FOR THEIR USE

This application claims the benefit under 35 U.S.C. 119(e) of provisional application 60/417,282, filed Oct. 9, 2002.

FIELD OF INVENTION

The present invention relates to the field of cloning vector plasmids, and to the use of cloning vector plasmids to build DNA constructs or transgenes.

DESCRIPTION OF THE PRIOR ART

The foundation of molecular biology is recombinant DNA technology, which can here be summarized as the modification and propagation of nucleic acids for the purpose of studying the structure and function of the nucleic acids and their protein products.

Individual genes, gene regulatory regions, subsets of genes, and indeed entire chromosomes in which they are contained, are all comprised of double-stranded anti-parallel sequences of nucleotides identified conventionally by the initials A, T, G, and C. These DNA sequences, as well as cDNA sequences derived from mRNA molecules, can be cleaved into distinct fragments, isolated, and inserted into a vector such as a bacterial plasmid to study the gene products. A plasmid is an extra-chromosomal piece of DNA that was originally derived from bacteria, and can be manipulated and reintroduced into a host bacterium for the purpose of study or production of a gene product. The DNA of a plasmid is similar to all chromosomal DNA, in that it is composed of the same A, T, G, and C nucleotides encoding genes and gene regulatory regions, however, it is a relatively small molecule comprised of less than approximately 30,000 base-pairs, or 30 kilobases (kb). In addition, the nucleotide base pairs of a double-stranded plasmid form a continuous circular molecule, also distinguishing plasmid DNA from that of chromosomal DNA.

Plasmids enhance the rapid exchange of genetic material between bacterial organisms and allow rapid adaptation to changes in environment, such as temperature, food supply, or other challenges. Any plasmid acquired must express a gene or genes that contribute to the survival of the host, or it will be destroyed or discarded by the organism since the maintenance of unnecessary plasmids would be a wasteful use of resources. A clonal population of cells contains identical genetic material, including any plasmids it might harbor. Use of a cloning vector plasmid with a DNA insert in such a clonal population of host cells will amplify the amount of the DNA of interest available. The DNA so cloned may then be isolated and recovered for subsequent manipulation in the steps required for building a DNA construct. Thus, it can be appreciated that cloning vector plasmids are useful tools in the study of gene fuction.

While some elements found in plasmids are naturally occurring, others have been engineered to enhance the usefulness of plasmids as DNA vectors. These include antibiotic- or chemical-resistance genes and a multiple cloning site (MCS), among others. Each of these elements has a role in the present invention, as well as in the prior art. Description of the role each element plays will highlight the limitations of the prior art and demonstrate the utility of the present invention.

A particularly useful plasmid-born gene that can be acquired by a host is one that would confer antibiotic resistance. In the daily practice of recombinant DNA technology, antibiotic resistance genes are exploited as positive or negative selection elements to preferentially enhance the culture and amplification of the desired plasmid over that of other plasmids.

In order to be maintained by a host bacterium a plasmid must also contain a segment of sequences that direct the host to duplicate the plasmid. Sequences known as the origin of replication (ORI) element direct the host to use its cellular enzymes to make copies of the plasmid. When such a bacterium divides, the daughter cells will each retain a copy or copies of any such plasmid. Certain strains of *E. coli* bacteria have been derived to maximize this duplication, producing upwards of 300 copies per bacterium. In this manner, the cultivation of a desired plasmid can be enhanced.

Another essential element in any cloning vector is a location for insertion of the genetic materials of interest. This is a synthetic element that has been engineered into "wild type" plasmids, thus conferring utility as a cloning vector. Any typical commercially-available cloning vector plasmid contains at least one such region, known as a multiple cloning site (MCS). A MCS typically comprises nucleotide sequences that may be cleaved by a single or a series of restriction endonuclease enzymes (hereafter referred to as "restriction enzymes"), each of which has a distinct recognition sequence and cleavage pattern. The so-called recognition sequences (which are referred to as restriction enzyme "sites") encoded in the DNA molecule comprise a double-stranded palindromic sequence. For some restriction enzymes, as few as 4-6 nucleotides are sufficient to provide a recognition site, while some restriction enzymes require a sequence of 8 or more nucleotides. The enzyme EcoR1, for example, recognizes the hexanucleotide sequence: $5'$G-A-A-T-T-C$3'$, wherein 5' indicates the end of the molecule known by convention as the "upstream" end, and 3' likewise indicates the "downstream" end. The complementary strand of the recognition sequence would be its anti-parallel strand, $3'$G-A-A-T-T-C-$5'$. Thus the double stranded recognition site can be represented within the larger double-stranded molecule in which it occurs as:

$$5'\ldots\ldots G-A-A-T-T-C\ldots\ldots 3'$$
$$3'\ldots\ldots C-T-T-A-A-G\ldots\ldots 5'$$

Like many other restriction enzymes, EcoR1 does not cleave exactly at the axis of dyad symmetry, but at positions four nucleotides apart in the two DNA strands between the nucleotides indicated by a "/":

$$5'\ldots\ldots G/A-A-T-T-C\ldots\ldots 3'$$
$$3'\ldots\ldots C-T-T-A-A/G\ldots\ldots 5'$$

such that double-stranded DNA molecule is cleaved and has the resultant configuration of nucleotides at the newly formed "ends":

This staggered cleavage yields fragments of DNA with protruding 5' termini. Because A-T and G-C pairs are spontaneously formed when in proximity with each other, protruding ends such as these are called cohesive or sticky ends. Any one of these termini can form hydrogen bonds with any other complementary termini cleaved with the same restriction enzyme. Since any DNA that contains a specific recognition sequence will be cut in the same manner as any other DNA containing the same sequence, those cleaved ends will be complementary. Therefore, the ends of any DNA molecules cut with the same restriction enzyme "match" each other in the way adjacent pieces of a jigsaw puzzle "match", and can be enzymatically linked together. It is this property that permits the formation of recombinant DNA molecules, and allows the introduction of foreign DNA fragments into bacterial plasmids, or into any other DNA molecule.

A further general principle to consider when building recombinant DNA molecules is that all restriction sites occurring within a molecule will be cut with a particular restriction enzyme, not just the site of interest. The larger a DNA molecule, the more likely it is that any restriction site will reoccur. Assuming that any restriction sites are distributed randomly along a DNA molecule, a tetranucleotide site will occur, on the average, once every $4^4$ (i.e., 256) nucleotides, whereas a hexanucleotide site will occur once every $4^6$ (i.e., 4096) nucleotides, and octanucleotide sites will occur once every $4^8$ (i.e., 114,688) nucleotides. Thus, it can be readily appreciated that shorter recognition sequences will occur frequently, while longer ones will occur rarely. When planning the construction of a transgene or other recombinant DNA molecule, this is a vital issue, since such a project frequently requires the assembly of several pieces of DNA of varying sizes. The larger these pieces are, the more likely that the sites one wishes to use occur in several pieces of the DNA components, making manipulation difficult, at best.

Frequently occurring restriction enzymes are herein referred to as common restriction enzymes, and their cognate sequences are referred to as common restriction sites. Restriction enzymes with cognate sequences greater than 6 nucleotides are referred to as rare restriction enzymes, and their cognate sites as rare restriction sites. Thus, the designations "rare" and common" do not refer to the relative abundance or availability of any particular restriction enzyme, but rather to the frequency of occurrence of the sequence of nucleotides that make up its cognate recognition site within any DNA molecule or isolated fragment of a DNA molecule, or any gene or its DNA sequence.

A second class of restriction endonuclease enzymes has recently been isolated, called homing endonuclease (HE) enzymes. HE enzymes have large, asymmetric recognition sites (12-40 base pairs). HE recognition sites are extremely rare. For example, the HE known as I-Scel has an 18 by recognition site (5' . . . TAGGGATAACAGGGTAAT . . . 3') (SEQ ID NO: 11), predicted to occur only once in every $7 \times 10^{10}$ base pairs of random sequence. This rate of occurrence is equivalent to only one site in 20 mammalian-sized genomes. The rare nature of HE sites greatly increases the likelihood that a genetic engineer can cut a final transgene product without disrupting the integrity of the transgene if HE sites were included in appropriate locations in a cloning vector plasmid.

Since a DNA molecule from any source organism will be cut in identical fashion by its cognate restriction enzyme, foreign pieces of DNA from any species can be cut with a restriction enzyme, inserted into a bacterial plasmid vector that was cleaved with the same restriction enzyme, and amplified in a suitable host cell. For example, a human gene may be cut in 2 places with EcoR1, the fragment with EcoR1 ends isolated and mixed with a plasmid that was also cut with EcoR1 in what is commonly known as a ligation reaction or ligation mixture. Under the appropriate conditions in the ligation mixture, some of the isolated human gene fragments will match up with the ends of the plasmid molecules. These newly joined ends can link together and enzymatically recircularize the plasmid, now containing its new DNA insert. The ligation mixture is then introduced into *E. coli* or another suitable host, and the newly engineered plasmids will be amplified as the bacteria divide. In this manner, a relatively large number of copies of the human gene may be obtained and harvested from the bacteria. These gene copies can then be further manipulated for the purpose of research, analysis, or production of its gene product protein.

Recombinant DNA technology is frequently embodied in the generation of so-called "transgenes". Transgenes frequently comprise a variety of genetic materials that are derived from one or more donor organisms and introduced into a host organism. Typically, a transgene is constructed using a cloning vector as the starting point or "backbone" of the project, and a series of complex cloning steps are planned to assemble the final product within that vector. Elements of a transgene, comprising nucleotide sequences, include, but are not limited to 1) regulatory promoter and/or enhancer elements, 2) a gene that will be expressed as a mRNA molecule, 3) DNA elements that provide mRNA message stabilization, 4) nucleotide sequences mimicking mammalian intronic gene regions, and 5) signals for mRNA processing such as the poly-A tail added to the end of naturally-occurring mRNAs. In some cases, an experimental design may require addition of localization signal to provide for transport of the gene product to a particular subcellular location. Each of these elements is a fragment of a larger DNA molecule that is cut from a donor genome, or, in some cases, synthesized in a laboratory. Each piece is assembled with the others in a precise order and 5'-3' orientation into a cloning vector plasmid.

The promoter of any gene may be isolated as a DNA fragment and placed within a synthetic molecule, such as a plasmid, to direct the expression of a desired gene, assuming that the necessary conditions for stimulation of the promoter of interest can be provided. For example, the promoter sequences of the insulin gene may be isolated, placed in a cloning vector plasmid along with a reporter gene, and used to study the conditions required for expression of the insulin gene in an appropriate cell type. Alternatively, the insulin gene promoter may be joined with the protein coding-sequence of any gene of interest in a cloning vector plasmid, and used to drive expression of the gene of interest in insulin-expressing cells, assuming that all necessary elements are present within the DNA transgene so constructed.

A reporter gene is a particularly useful component of some types of transgenes. A reporter gene comprises nucleotide sequences encoding a protein that will be expressed under the direction of a particular promoter of interest to which it is linked in a transgene, providing a measurable biochemical response of the promoter activity. A reporter gene is typically easy to detect or measure against the background of endogenous cellular proteins. Commonly used reporter genes include but are not limited to LacZ, green fluorescent protein, and luciferase, and other reporter genes, many of which are well-known to those skilled in the art.

Introns are not found in bacterial genomes, but are required for proper formation of mRNA molecules in mammalian cells. Therefore, any DNA construct for use in mammalian systems must have at least one intron. Introns may be isolated from any mammalian gene and inserted into a DNA construct, along with the appropriate splicing signals that allow mammalian cells to excise the intron and splice the remaining mRNA ends together.

An mRNA stabilization element is a sequence of DNA that is recognized by binding proteins that protect some mRNAs from degradation. Inclusion of an mRNA stabilization element will frequently enhance the level of gene expression from that mRNA in some mammalian cell types, and so can be useful in some DNA constructs or transgenes. An mRNA stabilization element can be isolated from naturally occurring DNA or RNA, or synthetically produced for inclusion in a DNA construct.

A localization signal is a sequence of DNA that encodes a protein signal for subcellular routing of a protein of interest. For example, a nuclear localization signal will direct a protein to the nucleus; a plasma membrane localization signal will direct it to the plasma membrane, etc. Thus, a localization signal may be incorporated into a DNA construct to promote the translocation of its protein product to the desired subcellular location.

A tag sequence may be encoded in a DNA construct so that the protein product will have an unique region attached. This unique region serves as a protein tag that can distinguish it from its endogenous counterpart. Alternatively, it can serve as an identifier that may be detected by a wide variety of techniques well known in the art, including, but not limited to, RT-PCR, immunohistochemistry, or in situ hybridization.

With a complex transgene, or with one that includes particularly large regions of DNA, there is an increased likelihood that there will be multiple recognition sites in these pieces of DNA. Recall that the recognition sequences encoding any one hexanucleotide site occur every 4096 bp. If a promoter sequence is 3000 bp and a gene of interest of 1500 bp are to be assembled into a cloning vector of 3000 bp, it is statistically very likely that many sites of 6 or less nucleotides will not be useful, since any usable sites must occur in only two of the pieces. Furthermore, the sites must occur in the appropriate areas of the appropriate molecules that are to be assembled. In addition, most cloning projects will need to have additional DNA elements added, thereby increasing the complexity of the growing molecule and the likelihood of inopportune repetition of any particular site. Since any restriction enzyme will cut at all of its sites in a molecule, if a restriction enzyme site reoccurs, all the inopportune sites will be cut along with the desired sites, disrupting the integrity of the molecule. Thus, each cloning step must be carefully planned so as not to disrupt the growing molecule by cutting it with a restriction enzyme that has already been used to incorporate a preceding element. And finally, when a researcher wishes to introduce a completed transgene into a mammalian organism, the fully-assembled transgene construct frequently must be linearized at a unique restriction site at at least one end of the transgene, thus requiring yet another unique site found nowhere else in the construct. Since most DNA constructs are designed for a single purpose, little thought is given to any future modifications that might need to be made, further increasing the difficulty for future experimental changes.

Traditionally, transgene design and construction consumes significant amounts of time and energy for several reasons, including the following:

1. There is a wide variety of restriction and HE enzymes available that will generate an array of termini, however most of these are not compatible with each other. Many restriction enzymes, such as EcoR1, generate DNA fragments with protruding 5' cohesive termini or "tails"; others (e.g., Pst1) generate fragments with 3' protruding tails, whereas still others (e.g., Bal1) cleave at the axis of symmetry to produce blunt-ended fragments. Some of these will be compatible with the termini formed by cleavage with other restriction and HE enzymes, but the majority of useful ones will not. The termini that can be generated with each DNA fragment isolation must be carefully considered in designing a DNA construct.
2. DNA fragments needed for assembly of a DNA construct or transgene must first be isolated from their source genomes, placed into plasmid cloning vectors, and amplified to obtain useful quantities. The step can be performed using any number of commercially-available or individually altered cloning vectors. Each of the different commercially available cloning vector plasmids were, for the most part, developed independently, and thus contain different sequences and restriction sites for the DNA fragments of genes or genetic elements of interest. Genes must therefore be individually tailored to adapt to each of these vectors as needed for any given set of experiments. The same DNA fragments frequently will need to be altered further for subsequent experiments or cloning into other combinations for new DNA constructs or transgenes. Since each DNA construct or transgene is custom made for a particular application with no thought or knowledge of how it will be used next, it frequently must be "retro-fitted" for subsequent applications.
3. In addition, the DNA sequence of any given gene or genetic element varies and can contain internal restriction sites that make it incompatible with currently available vectors, thereby complicating manipulation. This is especially true when assembling several DNA fragments into a single DNA construct or transgene.

Thus, there is a need for a system that would allow the user to rapidly assemble a number of DNA fragments into one molecule, despite redundancy of restriction sites found at the ends and within the DNA fragments. Such a system might also provide a simple means for rapidly altering the ends of the fragments so that other restriction sequences are added to them. Inclusion of single or opposing pairs of HE restriction sites would enhance the likelihood of having unique sites for cloning. A system that would also allow easy substitutions or removal of one or more of the fragments would add a level of versatility not currently available to users. Therefore, a "modular system, allowing one to insert or remove DNA fragments into or out of "cassette" regions flanked by rare restriction sites within the cloning vector would be especially useful, and welcome to the field of recombinant DNA technology.

BRIEF SUMMARY OF THE INVENTION

BRIEF DESCRIPTION OF THE DRAWINGS

FIG. 7 is a linear restriction site map illustrating an example of restriction enzyme sites that can be included in the SVP MCS.

FIG. 8 is a Shuttle Vector E (SVE) map.

BRIEF DESCRIPTION OF SEQUENCE LISTING

Figure 1:
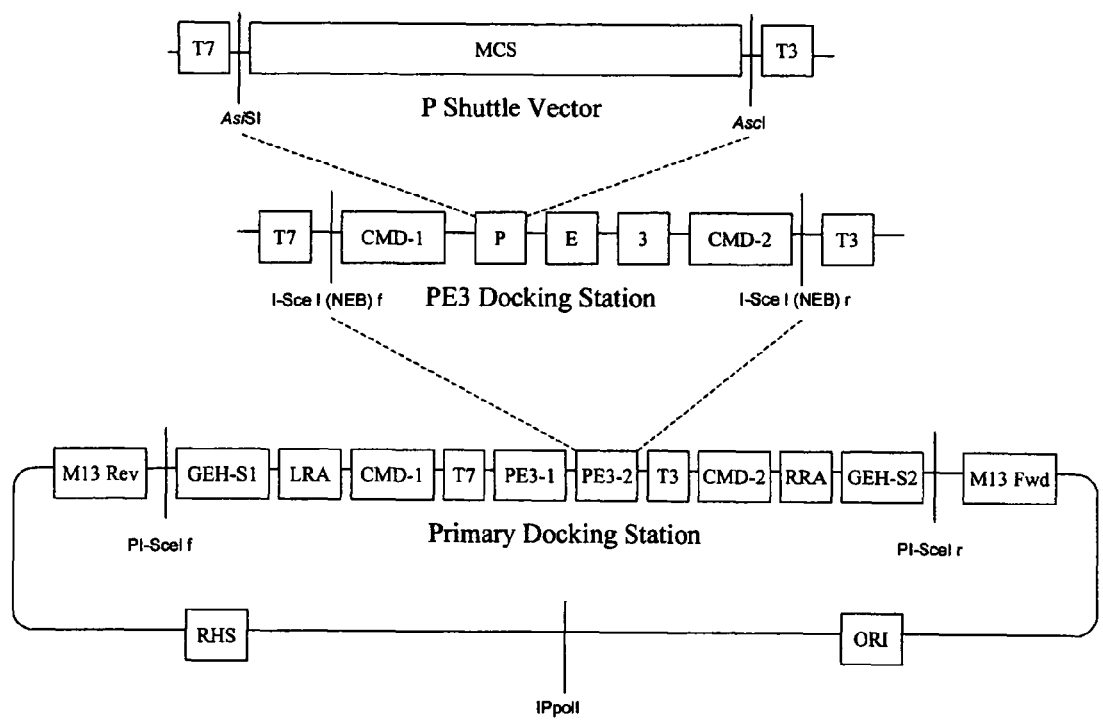
FIG. 1 is a linear map of the module concept of the invention.

SEQ:ID 01 is an example of a nucleotide sequence for a PE3 Docking Plasmid MCS.

SEQ:ID 02 is an example of a nucleotide sequence for a PE3 Docking Plasmid.

SEQ:ID 03 is an example of a nucleotide sequence for a Primary Docking Plasmid MCS.

SEQ:ID 04 is an example of a nucleotide sequence for a Primary Docking Plasmid.

SEQ:ID 05 is an example of a nucleotide sequence for a SVP Plasmid MCS.

SEQ:ID 06 is an example of a nucleotide sequence for a SVP Plasmid.

SEQ:ID 07 is an example of a nucleotide sequence for a SVE Plasmid MCS.

SEQ:ID 08 is an example of a nucleotide sequence for a SVE Plasmid.

SEQ:ID 09 is an example of a nucleotide sequence for a SV3 Plasmid MCS.

SEQ:ID 10 is an example of a nucleotide sequence for a SV3 Plasmid.

DEFINITIONS OF TERMS USED TO DESCRIBE THE INVENTION

As used herein, the terms "cloning vector" and "cloning vector plasmid" are used interchangeably to refer to a circular DNA molecule minimally containing an Origin of Replication, a means for positive selection of host cells harboring the plasmid such as an antibiotic-resistance gene; and a multiple cloning site.

As used herein, the term "Origin of Replication" (ORI) refers to nucleotide sequences that direct replication or duplication of a plasmid within a host cell As used herein, the term "multiple cloning site" refers to nucleotide sequences comprising restriction sites for the purpose of cloning DNA fragments into a cloning vector plasmid.

As used herein, the term "cloning" refers to the process of ligating a DNA molecule into a plasmid and transferring it an appropriate host cell for duplication during propagation of the host.

As used herein, the term "DNA construct" refers to a DNA molecule synthesized by consecutive cloning steps within a cloning vector plasmid, and is commonly used to direct gene expression in any appropriate cell host such as cultured cells in vitro, or a transgenic mouse in vivo. A transgene used to make such a mouse can also be referred to as a DNA construct, especially during the period of time when the transgene is being designed and synthesized.

As used herein, the term "Shuttle Vector" refers to a specialized cloning vector plasmid used in the invention to make an intermediate molecule that will modify the ends of a DNA fragment.

As used herein, the term "Docking Plasmid" refers to a specialized cloning vector plasmid used in the invention to assemble DNA fragments into a DNA construct.

As used herein, the terms "restriction endonuclease" or "restriction enzyme" refers to a member or members of a classification of catalytic molecules that bind a cognate sequence of DNA and cleave the DNA molecule at a precise location within that sequence.

As used herein, the terms "cognate sequence" or "cognate sequences" refer to the minimal string of nucleotides required for a restriction enzyme to bind and cleave a DNA molecule or gene.

As used herein, the term "DNA fragment" refers to any isolated molecule of DNA, including but not limited to a protein-coding sequence, reporter gene, promoter, enhancer, intron, exon, poly-A tail, multiple cloning site, nuclear localization signal, or mRNA stabilization signal, or any other naturally occurring or synthetic DNA molecule. Alternatively, a DNA fragment may be completely of synthetic origin, produced in vitro. Furthermore, a DNA fragment may comprise any combination of isolated naturally occurring and/or synthetic fragments.

As used herein, the terms "gene promoter" or "promoter" (P) refer to a nucleotide sequence required for expression of a gene.

As used herein, the term "enhancer region" refers to a nucleotide sequence that is not required for expression of a target gene, but will increase the level of gene expression under appropriate conditions.

As used herein, the term "reporter gene" refers to a nucleotide sequences encoding a protein useful for monitoring the activity of a particular promoter of interest.

As used herein, the term "chromatin modification domain" (CMD) refers to nucleotide sequences that interact with a variety of proteins associated with maintaining and/or altering chromatin structure.

As used herein, the term "poly-A tail" refers to a sequence of adenine (A) nucleotides commonly found at the end of messenger RNA (mRNA) molecules. A Poly-A tail signal is incorporated into the 3' ends of DNA constructs or transgenes to facilitate expression of the gene of interest.

As used herein, the term "intron" refers to the nucleotide sequences of a non-protein-coding region of a gene found between two protein-coding regions or exons.

As used herein, the term "untranslated region" (UTR) refers to nucleotide sequences encompassing the non-protein-coding region of an mRNA molecule. These untranslated regions can reside at the 5' end (5' UTR) or the 3' end (3' UTR) an mRNA molecule.

As used herein, the term "mRNA stabilization element" refers a sequence of DNA that is recognized by binding proteins thought to protect some mRNAs from degradation.

As used herein, the term "localization signal" (LOC) refers to nucleotide sequences encoding a signal for subcellular routing of a protein of interest.

As used herein, the term "tag sequence" (TAG) refers to nucleotide sequences encoding a unique protein region that allows it to be detected, or in some cases, distinguished from any endogenous counterpart.

As used herein, the term "primer site" refers to nucleotide sequences that serve as DNA templates onto which single-stranded DNA oligonucleotides can anneal for the purpose of initiating DNA sequencing, PCR amplification, and/or RNA transcription.

As used herein, the term "gene expression host selector gene" (GEH-S) refers to a genetic element that can confer resistance or toxicity to cells or organisms when treated with an appropriate antibiotic or chemical.

As used herein, the term "recombination arm" refers to nucleotide sequences that facilitate the homologous recombination between transgenic DNA and genomic DNA. Successful recombination requires the presence of a left recombination arm (LRA) and a right recombination arm (RRA) flanking a region of transgenic DNA to be incorporated into a host genome via homologous recombination.

As used herein, the term "pUC19" refers to a plasmid cloning vector well-known to those skilled in the art, and can be found in the NCBI Genbank database as Accession #L09137.

As used herein, the term "random nucleotide sequences" refers to any combination of nucleotide sequences that do not duplicate sequences encoding other elements specified as components of the same molecule.

As used herein, the term "unique" refers to any restriction endonuclease or HE site that is not found elsewhere within a DNA molecule.

DETAILED DESCRIPTION OF THE INVENTION

The present invention is a group of cloning vectors optimized to reduce the amount of manipulation frequently needed to assemble a variety of DNA fragments into a de novo DNA construct or transgene. The primary vector, herein referred to as a Docking Plasmid, contains a multiple cloning site (MCS) with 3 sets of rare restriction and/or HE sites arranged in a linear pattern. This arrangement defines a modular architecture that allows the user to assemble multiple inserts into a single transgene construct without disturbing the integrity of DNA elements already incorporated into the Docking Plasmid in previous cloning steps.

Two recognition sites for at least three HE are placed in opposite orientation to flank three modular regions for the purpose of creating a gene cassette acceptor site that cannot self-anneal. Because HE sites are asymmetric and non-palindromic, it is possible to generate non-complementary protruding 3' cohesive tails by placing two HE recognition sites in opposite orientation. Thus, the HE I-SceI cuts its cognate recognition site as indicated by "/":

```
                                    (SEQ ID NO: 11)
5'...TAGGGATAA/CAGGGTAAT...3'

(SEQ ID NO: 12)
3'...ATCCC/TATTGTCCCATTA...5'
```

The reverse placement of a second site within an MCS would generate two non-complementary cohesive protruding tails:

```
                                    (SEQ ID NO: 13)
5'...TAGGGATAA   CCCTA...3'

(SEQ ID NO: 13)
3'...ATCCC   AATAGGGAT...5'
```

This is particularly useful when it is necessary to subclone larger transgenes into a vector. Due to the size of the insert, it is thermodynamically more favorable for a vector to self anneal rather than accept a large insert. The presence of non-complementary tails generated by this placement of restriction sites provides chemical forces to counteract the thermodynamic inclination for self-ligation.

The asymmetric nature of most HE protruding tails also creates a powerful cloning tool when used in combination with the BstX I restriction enzyme site (5'CCANNNNN/NTGG 3') (SEQ ID NO: 14). The sequence-neutral domain of BstX I can be used to generate compatible cohesive ends for two reverse-oriented HE protruding tails, while precluding self-annealing.

The secondary vectors of the invention, herein known as Shuttle vectors, contain multiple cloning sites with common restriction sites flanked by rare restriction and/or HE sites. The shuttle vectors are designed for cloning fragments of DNA into the common restriction sites between the rare sites. The cloned fragments can subsequently be released by cleavage at the rare restriction or HE site or sites, and incorporated into the Docking Plasmid using the same rare restriction and/or HE site or sites found in the shuttle vectors.

Thus, unlike conventional cloning vectors, the design of the MCS allows "cassettes" or modules of DNA fragments to be inserted into the modular regions of the Docking Plasmid. Likewise, each can be easily removed using the same rare restriction and/or HE enzymes, and replaced with any other DNA fragment of interest. This feature allows the user to change the direction of an experimental project quickly and easily without having to rebuild the entire DNA construct. Thus, the cloning vector plasmids of the present invention allow the user to clone a DNA fragment into an intermediate vector using common restriction sites, creating a cassette-accepting module, and to then transfer that fragment to the desired modular spot in the final construct by means of rare restriction sites. Furthermore, it allows future alterations to the molecule to replace individual modules in the Docking Plasmid with other cassette modules. The following descriptions highlight distinctions of the present invention compared with the prior art.

Individual components of a transgene (the promoter enhancer P, expressed protein E, and/or 3' regulatory region 3) can be assembled as modules transferred from shuttle vectors into the PE3 Docking Station Plasmid. If higher orders of complexity are needed, the assembled transgenes, or other nucleotide sequences, can then be transferred into a Primary Docking Plasmid. Each of the five types of cloning vector plasmids will be explained in greater detail to provide an understanding of the components incorporated into each, beginning with the more complex PE3 Docking Station Plasmid and the Primary Docking Plasmid.

Figure 2:
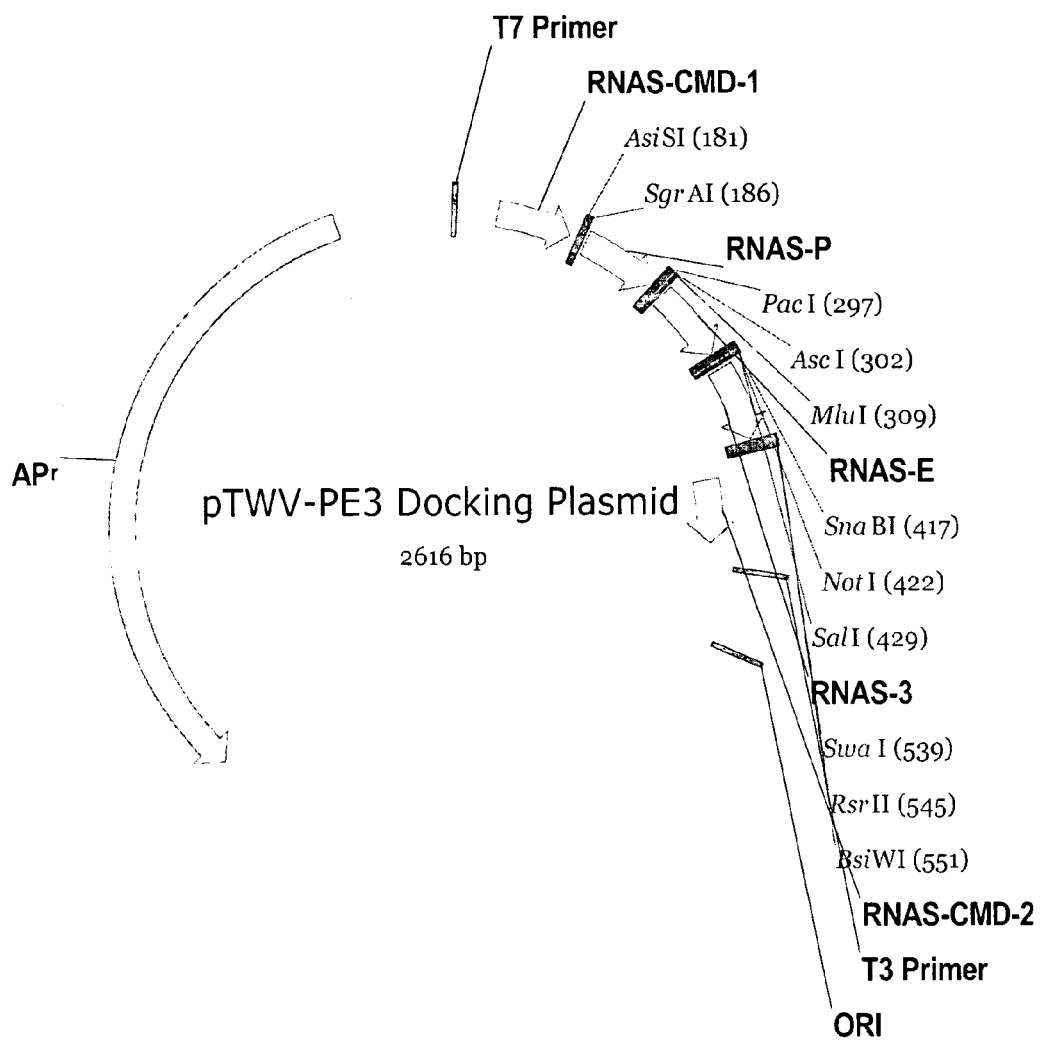
FIG. 2 is a Docking Plasmid map.

The PE3 Docking Plasmid (FIG. 2) comprises a pUC19 backbone with the following modifications, wherein the sequences are numbered according to the pUC19 Genbank sequence file, Accession #L09137:

1. Only sequences from 806 to 2617 (Afl3-Aat2) are used in the Docking Plasmid,
2. The BspH1 site at 1729 in pUC19 is mutated from TCATGA to GCATGA,
3. The Acl1 site at 1493 in pUC19 is mutated from AACGTT to AACGCT,
4. The Acl1 site at 1120 in pUC19 is mutated from AACGTT to CACGCT,
5. The Ahd1 site in pUC19 is mutated from GACNNNNNGTC (SEQ ID NO: 17) to CACNNNNNGTC (SEQ ID NO: 18),

| BstX I (I-Sce I Fwd.) | I-Sce I Forward | I-Sce I Reverse | BxtX I (I-Sce I Rev.) |
|---|---|---|---|
| 5'-CCAGATAA | CAGGGTAAT//ATTACCCTGTTAT | | GTGG-3' (SEQ ID NO: 15) |
| 3'-GGTC | TATTGTCCCATTA//TAATGGGAC | | AATACACC-5' (SEQ ID NO: 16) |

6. Sequences encoding BspH1/I-Ppo 1/BspH1 are inserted at the only remaining BspH1 site in pUC19 following the mutation step 2 in the list above.

Figure 3:
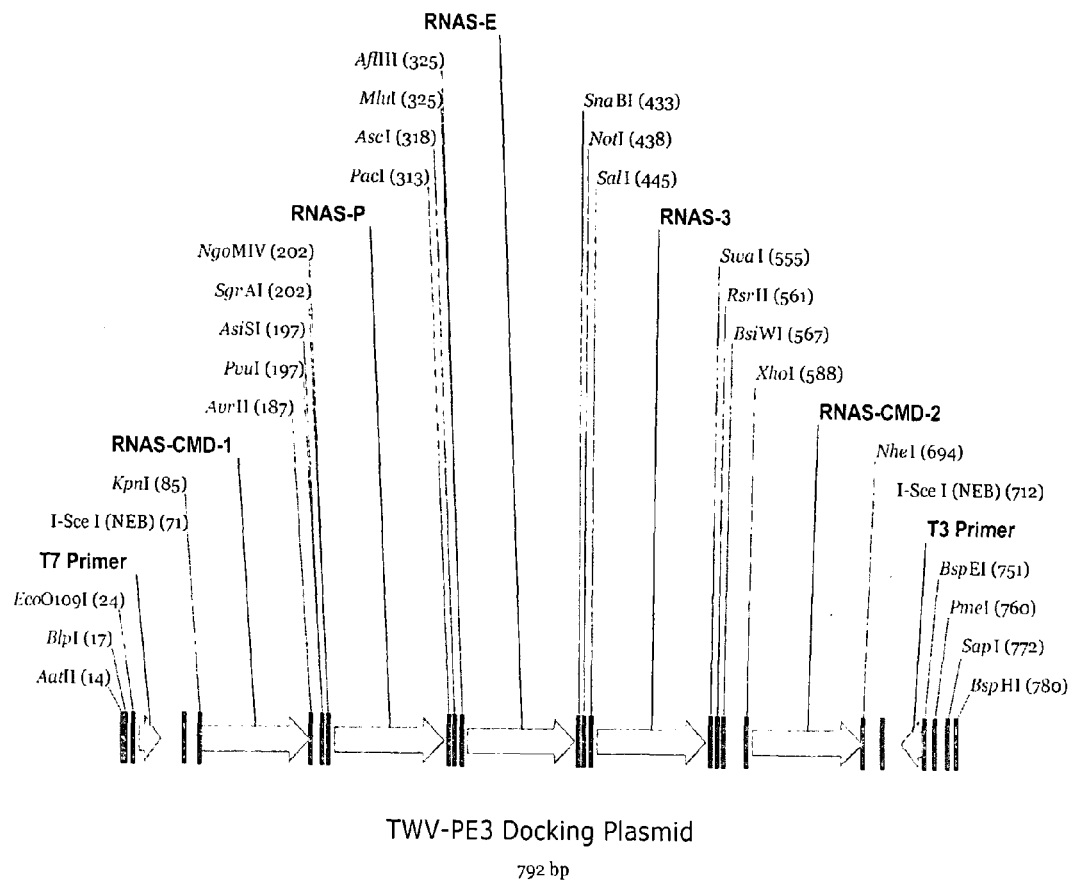
FIG. 3 is a linear restriction map illustrating an example of restriction enzyme sites that can be included in the Docking Plasmid MCS.

The multiple cloning site (MCS) in the PE3 Docking Plasmid (FIG. 3) comprises the following sequential elements, in the order listed:

1. Three non-variable and unique common restriction sites that define a 5' insertion site for the mutated pUC19 vector described above (for example, Aat II, Blp I, and EcoO109 I),
2. A T7 primer site.
3. A unique HE site (for example, I-SceI (forward orientation)),
4. A pair of non-variable and unique, common restriction sites flanking random nucleotide sequences that can serve as a chromatin modification domain acceptor module (RNAS-CMD-1) (for example, Kpn I and Avr II),
5. A fixed grouping of non-variable rare restriction sites that define the 5' portion of the promoter module (for example, AsiS I and SgrA I),
6. Random nucleotide sequences that can serve as a Promoter/intron acceptor module (RNAS-P),
7. A fixed grouping of non-variable rare restriction sites that define the shared junction between the 3' portion of the Promoter/intron module and the 5' portion of the Expression module (for example, PacI, AscI, and MluI),
8. Random nucleotide sequences that can serve as an expression acceptor module (RNAS-E),
9. A fixed grouping of non-variable rare restriction sites that define the junction of the 3' portion of the Expression module and the 5' portion of the 3' Regulatory module (for example, SnaB I, Not I, and Sal I),
10. Random nucleotide sequences that can serve as a 3' regulatory domain acceptor module (RNAS-3),
11. A fixed grouping of non-variable rare restriction sites that define the 3' portion of the 3' Regulatory module (for example, Swa I, Rsr II, and BsiW I),
12. A pair of non-variable and unique, common restriction sites flanking a random nucleotide sequence of DNA that can serve as a chromatin modification domain acceptor module (RNAS-CMD-2) (for example, Xho I and Nhe I),
13. A unique HE site in reverse orientation that is identical to that in item 3, above,
14. A T3 primer site in reverse orientation, and
15. Four non-variable and unique common restriction sites that define a 3' insertion site for the mutated pUC19 vector described above (for example, BspE I, Pme I, Sap I, and BspH I).

Figure 4:
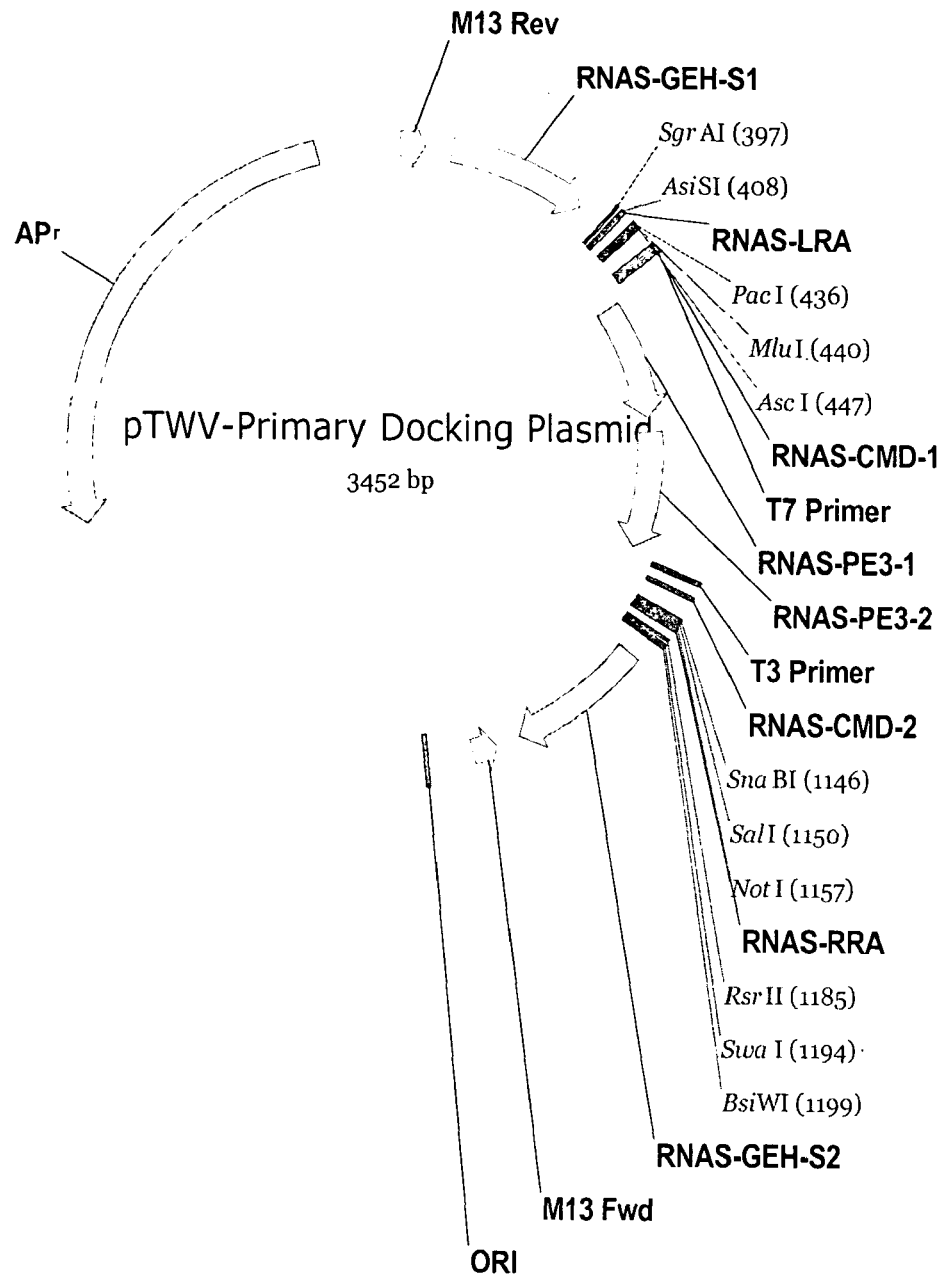
FIG. 4 is a Primary Docking Plasmid map.
Figure 5:
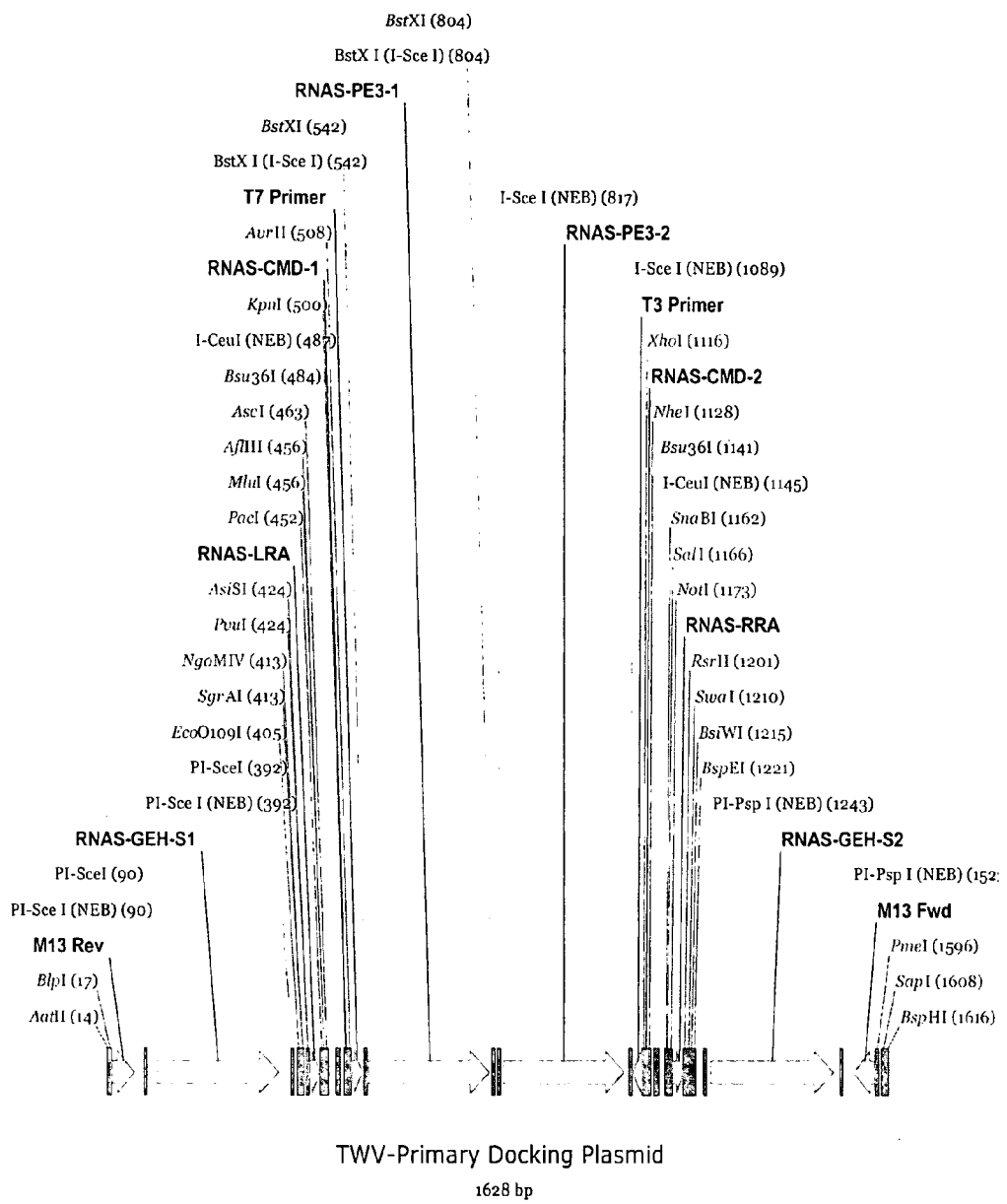
FIG. 5 is a linear restriction site map illustrating an example of restriction enzyme sites that can be included in the Primary Docking Plasmid MCS.

The Primary Docking Plasmid (FIG. 4) can be used to assemble two completed transgenes that are first constructed in PE3 Docking Station Plasmids, or two homology arms needed to construct a gene-targeting transgene, or to introduce two types of positive or negative selection elements. The multiple cloning site (MCS) in the Primary Docking Plasmid (FIG. 5) comprises the following sequential elements, in the order listed:

1. Two non-variable and unique common restriction sites that define a 5' insertion site for the mutated pUC19 vector described above (for example, Aat II and Blp I),
2. An M13 Rev. primer site,
3. A pair of unique HE sites in opposite orientation flanking a random nucleotide sequence of DNA that can serve as a genome expression host selector gene acceptor module (RNAS-GEH-S1) (for example, PI-SceI (forward orientation) and PI-SceI (reverse orientation)),
4. A non-variable and unique, common restriction site that allows cloning of a shuttle vector module downstream of the HE pair (for example, Eco0109I),
5. A fixed grouping of non-variable rare restriction sites that define the 5' portion a Left Recombination Arm module (for example, SgrA I and AsiS I),
6. Random nucleotide sequences that can serve as a Left Recombination Arm acceptor module (RNAS-LRA),
7. A fixed grouping of non-variable rare restriction sites that define the 3' portion of the Left Recombination Arm acceptor module (for example, PacI, MluI, and AscI),
8. A unique HE site (for example, I-Ceu I (forward orientation)),
9. A pair of non-variable and unique, common restriction sites flanking a random nucleotide sequence of DNA that can serve as a chromatin modification domain acceptor module (RNAS-CMD-1) (for example, Kpn I and Avr II),
10. A T7 primer site,
11. A pair of unique BstX I sites in opposite orientation (wherein the variable nucleotide region in the BstX I recognition site is defined by nucleotides identical to the non-complementary tails generated by the ordering of two identical HE recognition sites arranged in reverse-complement orientation; for example, PI-SceI (forward orientation) and PI-SceI (reverse orientation)) flanking a random nucleotide sequence of DNA that can serve as a complex transgene acceptor module (RNAS-PE3-1),
12. A pair of unique HE sites in opposite orientation flanking a random nucleotide sequence of DNA that can serve as a complex transgene acceptor module (RNAS-PE3-2) (for example, I-SceI (forward orientation) and I-SceI (reverse orientation)),
13. A T3 primer site in reverse-orientation,
14. A pair of non-variable and unique, common restriction sites flanking a random nucleotide sequence of DNA that can serve as a chromatin modification domain acceptor module (RNAS-CMD-2) (for example, Xho I and Nhe I),
15. A unique HE site in reverse orientation that is identical to that in item 8 above,
16. A fixed grouping of non-variable rare restriction sites that define the 5' portion a Right Recombination Arm module (for example, SnaB I, Sal I, and Not I),
17. Random nucleotide sequences that can serve as a Right Recombination Arm acceptor module (RNAS-RRA),
18. A fixed grouping of non-variable rare restriction sites that define the 3' portion of the Right Recombination Arm acceptor module (for example, Rsr II, Swa I, and BsiW I),
19. A non-variable and unique, common restriction site that allows cloning of a shuttle vector module upstream of an HE pair (for example, BspE I),
20. A pair of unique HE sites in opposite orientation flanking a random nucleotide sequence of DNA that can serve as a genome expression host selector gene acceptor module (RNAS-GEH-S2) (for example, PI-Psp I (forward orientation) and PI-Psp I (reverse orientation)),
21. An M13 Forward primer site placed in reverse orientation,
22. Three non-variable and unique common restriction sites that define a 3' insertion site for the mutated pUC19 vector described above (for example, Pme I, Sap I, and BspH I).

Three cloning vector plasmids of the invention are known as Shuttle Vectors. The Shuttle Vectors, like the PE3 and Primary Docking Plasmids, are also constructed from a pUC19 backbone. Just like the PE3 and Primary Docking Plasmids, each Shuttle Vector has the same modifications to the pUC19 backbone listed as 1 through 6, above. The individual Shuttle Vectors (SV) are identified as Shuttle Vector Promoter/intron (P), Shuttle Vector Expression (E), and Shuttle Vector 3'Regulatory (3); henceforth SVP, SVE, and SV3, respectively. Each is described more fully below.

Shuttle Vector P (SVP)

Figure 6:
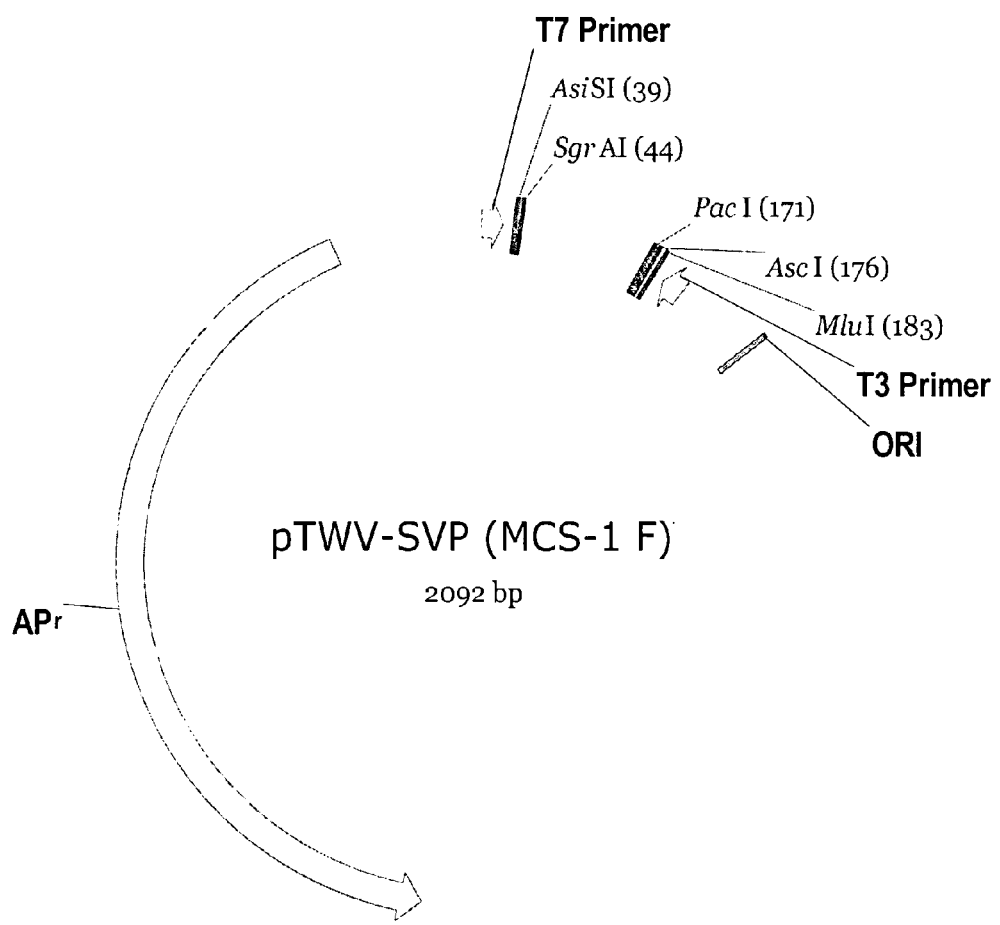
FIG. 6 is a Shuttle Vector P (SVP) plasmid map.

SVP is a cloning vector plasmid that one can be used to prepare promoter and intron sequences for assembly into a transgene construct (FIG. 6). An example of an SVP Plasmid can comprise the following sequential elements in the MCS (FIG. 7), in the order listed:

1. Two non-variable and unique, common restriction sites that define a 5' insertion site for the mutated pUC19 vector described above (for example, AatII and BlpI),
2. A T7 primer site,
3. A non-variable and unique, common restriction site that allows efficient cloning of a shuttle vector module downstream of the T7 primer site (for example, Eco0109I),
4. A fixed grouping of non-variable rare restriction sites that define the 5' portion of the promoter module (for example, AsiSI and SgrAI),
5. A variable MCS comprising any grouping of common or rare restriction sites that are unique to the shuttle vector (for example, the series of restriction sites illustrated in FIG. 7),
6. A fixed grouping of non-variable rare restriction sites that define the 3' portion of the promoter module (for example, PacI, AscI, and MluI)
7. A non-variable and unique, common restriction site that allows efficient cloning of a shuttle vector module upstream of the T3 primer site (for example, BspEI)
8. A reverse-orientation T3 primer site, and
9. Two non-variable and unique, common restriction sites that define a 3' insertion site for the mutated pUC19 vector described above (for example, PmeI and SapI).

Shuttle Vector E (SVE)

Figure 8:
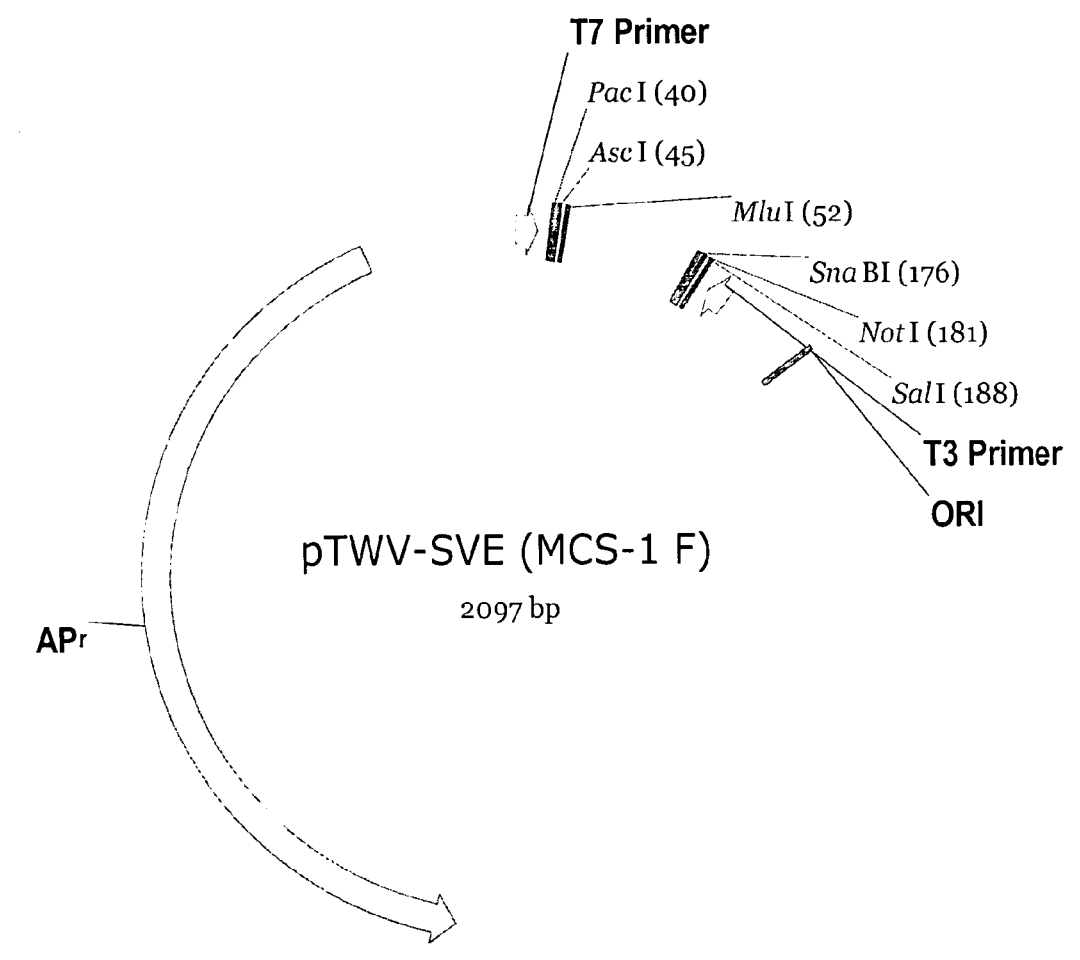
Figure 9:
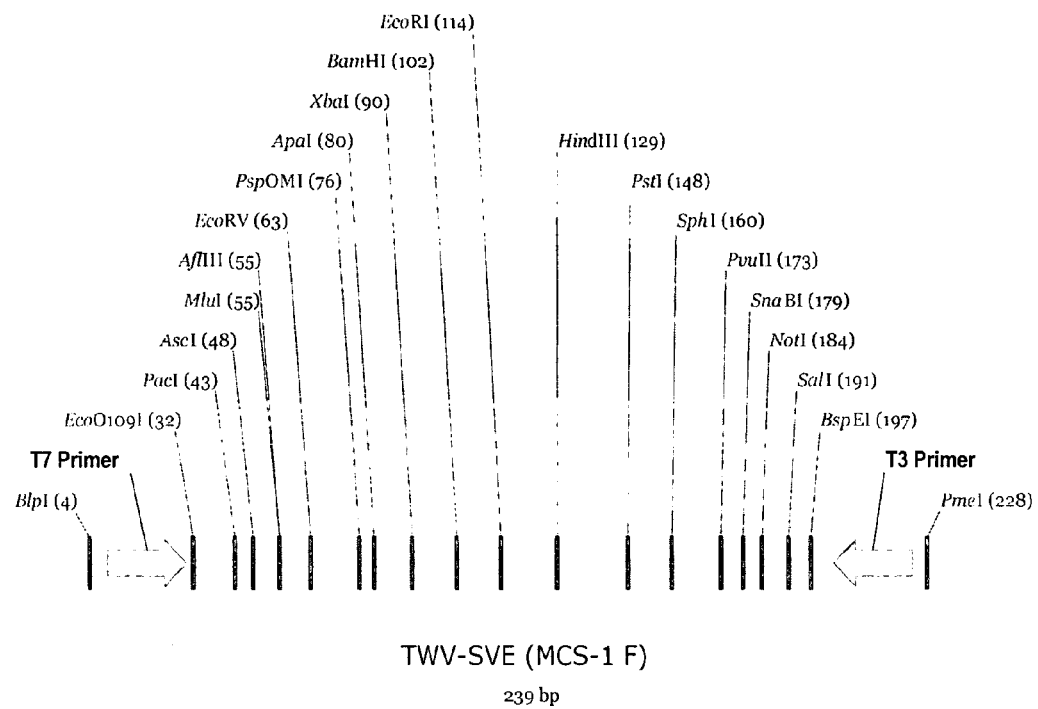
FIG. 9 is a linear restriction site map illustrating an example of restriction enzyme sites that can be included in the SVE MCS.

This is a cloning vector plasmid that can be used to prepare sequences to be expressed by the transgene for assembly into a transgene construct (FIG. 8). An example of an SVE plasmid can comprise the following sequential elements in the MCS (FIG. 9), in the order listed:

1. Two non-variable and unique, common restriction sites that define a 5' insertion site for the mutated pUC19 vector described above (for example, AatII and Blp \I),
2. A T7 primer site,
3. A non-variable and unique, common restriction site that allows efficient cloning of a shuttle vector module downstream of the T7 primer site (for example, Eco0109\I),
4. A fixed grouping of non-variable rare restriction sites that define the 5' portion of the expression module (for example, PacI, AscI, and MluI),
5. A variable MCS consisting of any grouping of common or rare restriction sites that are unique to the shuttle vector (for example, the series of restriction sites illustrated in FIG. 9),
6. A fixed grouping of non-variable rare restriction sites that define the 3' portion of the expression module (for example, SnaBI, NotI, and SalI),
7. A non-variable and unique, common restriction site that allows efficient cloning of a shuttle vector module upstream of the T3 primer site (for example, BspEI)
8. A reverse-orientation T3 primer site, and
9. Two non-variable and unique, common restriction sites that define a 3' insertion site for the 30 mutated pUC19 vector described above (for example, PmeI and SapI).

Shuttle Vector 3 (SV3)

Figure 10:
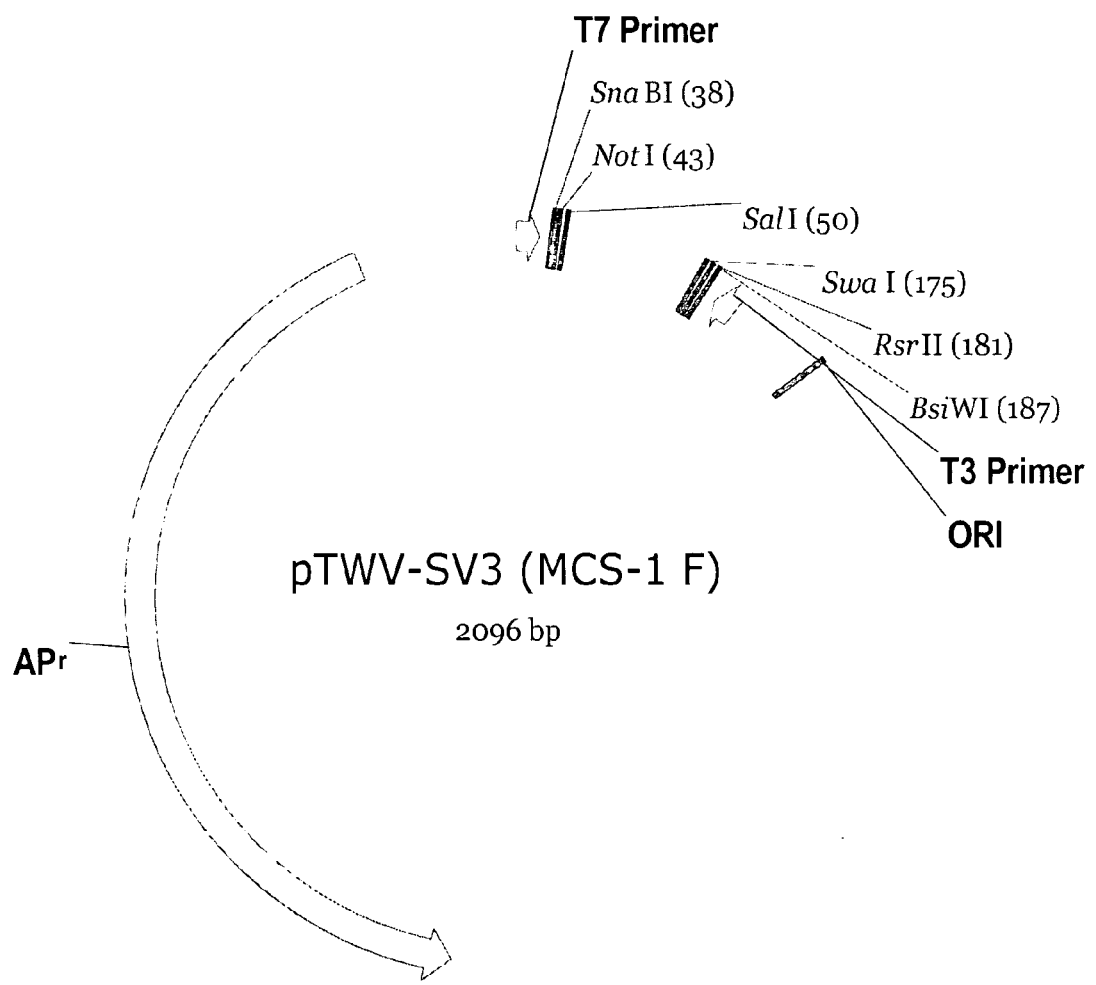
FIG. 10 is a Shuttle Vector 3' (SV3) map.
Figure 11:
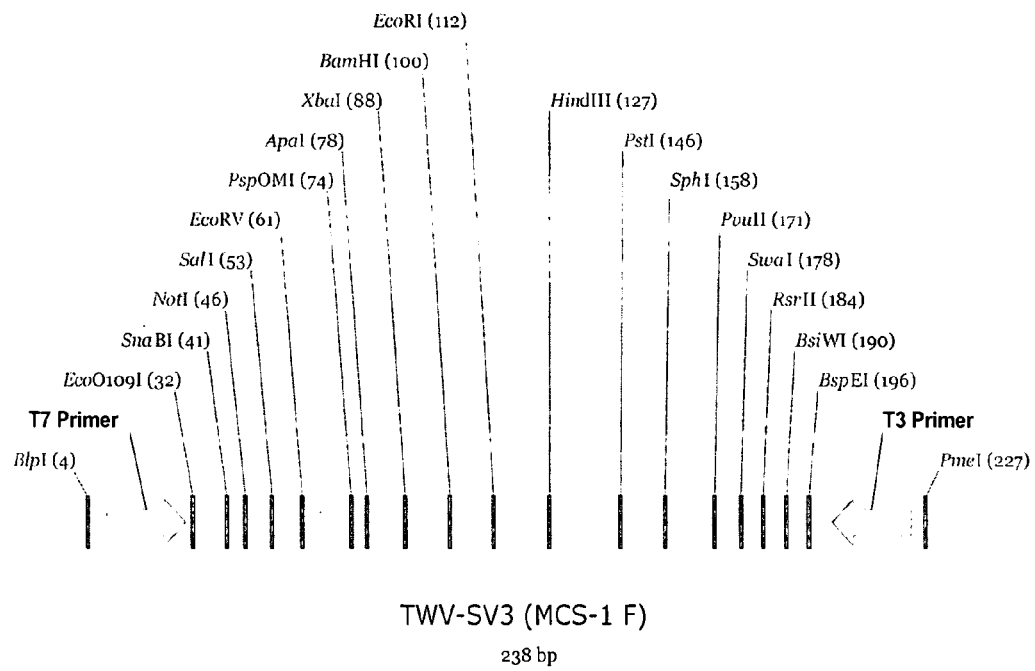
FIG. 11 is a linear restriction site map illustrating an example of restriction enzyme sites that can be included in the SV3 MCS.

This is a cloning vector plasmid that can be used to prepare 3' regulatory sequences for assembly into a transgene construct (FIG. 10). An example of an SV3 plasmid can comprise the following elements in the MCS (FIG. 11), in the order listed:

1. Two non-variable and unique, common restriction sites that define a 5' insertion site for the mutated pUC19 vector described above (for example, AatII and BlpI),
2. A T7 primer site,
3. A non-variable and unique, common restriction site that allows efficient cloning of a shuttle vector module downstream of the T7 primer (for example, Eco0109I),
4. A fixed grouping of non-variable rare restriction sites that define the 5' portion of the 3' regulatory module (for example, SnaBI, NotI, and SalI),
5. A variable MCS consisting of any grouping of common or rare restriction sites that are unique to the shuttle vector (for example, the series of restriction sites illustrated in FIG. 11),
6. A fixed grouping of non-variable rare restriction sites that define the 3' portion of the 3' regulatory module (for example, SwaI, RsrII, and BsiWI),
7. A non-variable and unique, non-rare restriction site that allows efficient cloning of a shuttle vector module upstream of the T3 primer site (for example, BspEI),
8. A reverse-orientation T3 primer site, and
9. Two non-variable and unique, non-rare restriction sites that define a 3' insertion site for the mutated pUC19 vector described above (for example, PmeI and SapI).

While the present invention discloses methods for building transgenes in plasmid cloning vectors, similar methods can be used to build transgenes in larger extrachromosomal DNA molecules such as cosmids or artificial chromosomes, including bacterial artificial chromosomes (BAC). The wide variety of genetic elements that can be incorporated into the plasmid cloning vectors also allow transfer of the final transgene products into a wide variety of host organisms with little or no further manipulation.

As an example of the method of practicing the present invention, a transgene can be constructed containing these elements:

1. Nucleotide sequences of the human promoter for surfactant protein C (SP—C),
2. Sequences encoding the protein product of the mouse gene granulocyte-macrophage colony-stimulating factor-receptor beta c (GMRβc)
3. Rabbit betaglobin intron sequences, and
4. SV40 poly-A signal.

The SP—C sequences contain internal BamH1 sites, and can be released from its parental plasmid only with Not1 and EcoR1. GMRβc has an internal Not1 site, and can be cut from its parental plasmid with BamH1 and Xho1. The rabbit betaglobin intron sequences can be cut out of its parental plasmid with EcoR1. The SV-40 poly-A tail can be cut from its parental plasmid with Xho1 and Sac1. Because of redundancy of several of restriction sites, none of the parental plasmids can be used to assemble all the needed fragments.

The steps used to build the desired transgene in the PE3 Docking Plasmid invention are as follows.

1. Since Not1 and PspOM1 generate compatible cohesive ends, the human SP—C promoter sequences are excised with Not1 and EcoR1 and cloned into the PspOM1 and EcoR1 sites of Shuttle Vector P. The product of this reaction is called pSVP-SPC
2. Following propagation and recovery steps well known to those skilled in the art, the rabbit betaglobin intron sequences are cloned into the EcoR1 site of pSVP-SPC. Orientation of the intron in the resultant intermediate construct is verified by sequencing the product, called pSVP-SPC-rβG.
3. The promoter and intron are excised and isolated as one contiguous fragment from pSVP-SPC-rβG using AsiS1 and Asc1. Concurrently, the PE3 Docking Plasmid is cut with AsiS1 and Asc1 in preparation for ligation with the promoter/intron segment. The promoter/intron fragment is ligated into the Docking Plasmid, propagated, and recovered.

4. The Xho1 site of the GMRβc fragment is filled in to create a blunt 3' end, using techniques well known to those skilled in the art. It is then cloned into the BamH1 site and the blunt-ended Pvu2 site of pSVP-SPC-rβG. The resultant plasmid (pDP-SPC-GMRβc-rβG) was propagated and recovered.

5. The final cloning step is the addition of the SV-40 Poly-A tail. The SV40-polyA fragment is cut out with Xho1 and Sac1, as is the recipient vector pDS1-SPC-GMRβc-rbβG. Both pieces of DNA are gel purified and recovered. A ligation mix is prepared with a 10:1 molar ratio of SV-40polyA to pDS1-SPC-GMRβc-rβG. The ligation products are propagated and harvested. The new plasmid, pDS1-SPC-GMRβc-rβG-pA contains all elements required for the transgene, including a unique restriction site at the 3' end with which the entire pDS1-SPC-GMRβc-rβG-pA plasmid can be linearized for transfection into eukaryotic cells or microinjection into the pronucleus of a fertilized ovum.

What is claimed is:

1. A plasmid comprising a polynucleotide sequence comprising the following elements:
   (a) a homing endonuclease site,
   (b) a set of rare restriction sites,
   (c) a region of random nucleotide sequence that can serve as a promoter/intron acceptor module,
   (d) a set of rare restriction sites;
   (e) a region of random nucleotide sequence that can serve as an expression acceptor module,
   (f) a set of rare restriction sites;
   (g) a region of random nucleotide sequence that can serve as a 3' regulatory domain acceptor module,
   (h) a set of rare restriction sites, and
   (i) a homing endonuclease site in reverse orientation that is identical to the homing endonuclease site in element (a), wherein elements (a) through (i) are arranged sequentially in the 5' to 3'direction of said plasmid.

2. The plasmid of claim 1, further comprising AatII, BlpI and/or Eco0109 I restriction sites 5' of the homing endonuclease site (a).

3. The plasmid of claim 2, further comprising BspEI, PmeI, SapI and/or BspHI restriction sites 3' of the homing endonuclease site (i).

4. The plasmid of claim 1, wherein said set of restriction sites of element (b) comprises an AsiSI restriction site and/or a SgrA I restriction site.

5. The plasmid of claim 1, wherein said set of restriction sites of element (d) comprises a PacI restriction site and/or an AscI restriction site.

6. The plasmid of claim 1, wherein said set of restriction sites of element (f) comprises a NotI restriction site.

7. The plasmid of claim 1, wherein said set of restriction sites of element (h) comprises a SwaI restriction site and/or an RsrII restriction site.

8. The plasmid of claim 1, wherein
   said set of restriction sites of element (b) comprises an AsiSI restriction site and/or an SgrA I restriction site;
   said set of restriction sites of element (d) comprises a PacI restriction site and/or an AscI restriction site;
   said set of restriction sites of element (f) comprises a NotI restriction site; and
   said set of restriction sites of element (h) comprises a SwaI restriction site and/or an RsrII restriction site.

9. The plasmid of claim 6, wherein said set of restriction sites of element (f) further comprises a Sna BI restriction site.

10. The plasmid of claim 1, wherein said homing endonuclease sites are I-SceI or PI-Sce I restriction sites.

11. A composition for cloning transgenes, said composition comprising:
   (a) a plasmid according to claim 1 that contains a transgene comprising a promoter module, an expression module and a 3' regulatory module; and
   (b) a plasmid that accepts said transgene.

12. The plasmid of claim 1, wherein the restriction sites of elements (b), (d), (f) and (h) are AsiS I, SgrA I, PacI, AscI, SnaBI, Not I, Swa I or RsrII restriction sites.

* * * * *

SEQUENCE LISTING

```
<160> NUMBER OF SEQ ID NOS: 18

<210> SEQ ID NO 1
<211> LENGTH: 3452
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: modified_base
<222> LOCATION: (98)..(347)
<223> OTHER INFORMATION: a, c, g, t, unknown or other
<220> FEATURE:
<221> NAME/KEY: modified_base
<222> LOCATION: (411)..(430)
<223> OTHER INFORMATION: a, c, g, t, unknown or other
<220> FEATURE:
<221> NAME/KEY: modified_base
<222> LOCATION: (530)..(779)
<223> OTHER INFORMATION: a, c, g, t, unknown or other
<220> FEATURE:
<221> NAME/KEY: modified_base
<222> LOCATION: (810)..(1059)
<223> OTHER INFORMATION: a, c, g, t, unknown or other
<220> FEATURE:
<221> NAME/KEY: modified_base
<222> LOCATION: (1163)..(1182)
<223> OTHER INFORMATION: a, c, g, t, unknown or other
<220> FEATURE:
<221> NAME/KEY: modified_base
<222> LOCATION: (1240)..(1489)
<223> OTHER INFORMATION: a, c, g, t, unknown or other

<400> SEQUENCE: 1
tgagcagcgg ataacaattt cacacaggaa acagctatga ccatgattac tctgtagcat      60
ctatgtcggg tgcggagaaa gaggtaatga aatggcannn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnntgc catttcatta      360 cctctttctc cgcacccgac atagataggc cctgcgccgg cggcgatcgc nnnnnnnnnn     420
nnnnnnnnnn ttaattaaac gcgtggcgcg cctaactata acggtcctaa ggtagcgagg     480
taccgctggc cctagggtaa tacgactcac tatagggcca cataagtggn nnnnnnnnnn    540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
```

```
nnnnnnnnnn nnnnnnnnnn nnnnnnnnnn nnnnnnnnnn nnnnnnnnnn nnnnnnnnnc    780
cacttatgtg gtagggataa cagggtaatn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnna ttaccctgtt atccctatcc   1080
ctttagtgag ggttaattct cgaggcagga gctagctcgc taccttagga ccgttatagt   1140
tatacgtagt cgacgcggcc gcnnnnnnnn nnnnnnnnnn nncggtccga tttaaatcgt   1200
acgtccggat ggcaaacagc tattatgggt attatgggtn nnnnnnnnnn nnnnnnnnnn   1260
nnnnnnnnnn nnnnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnna cccataatac   1500
ccataatagc tgtttgccag ctacagagtt tactggccgt cgttttacaa cgtcgtgact   1560
gggaaaaccc tggcggttta aacgctcttc cgcttccttc atgtgagcaa aaggccagca   1620
aaaggccagg aaccgtaaaa aggccgcgtt gctggcgttt ttccataggc tccgcccccc   1680
tgacgagcat cacaaaaatc gacgctcaag tcagaggtgg cgaaacccga caggactata   1740
aagataccag gcgtttcccc ctggaagctc cctcgtgcgc tctcctgttc cgaccctgcc   1800
gcttaccgga tacctgtccg cctttctccc ttcgggaagc gtggcgcttt ctcatagctc   1860
acgctgtagg tatctcagtt cggtgtaggt cgttcgctcc aagctgggct gtgtgcacga   1920
accccccgtt cagcccgacc gctgcgcctt atccggtaac tatcgtcttg agtccaaccc   1980
ggtaagacac gacttatcgc cactggcagc agccactggt aacaggatta gcagagcgag   2040
gtatgtaggc ggtgctacag agttcttgaa gtggtggcct aactacggct acactagaag   2100
gacagtattt ggtatctgcg ctctgctgaa gccagttacc ttcggaaaaa gagttggtag   2160
ctcttgatcc ggcaaacaaa ccaccgctgg tagcggtggt ttttttgttt gcaagcagca   2220
gattacgcgc agaaaaaaag gatctcaaga agatcctttg atcttttcta cggggtctga   2280
cgctcagtgg aacgaaaact cacgttaagg gattttggtc atgataacta tgactctctt   2340
aaggtagcca aattcatgag attatcaaaa aggatcttca cctagatcct tttaaattaa   2400
aaatgaagtt ttaaatcaat ctaaagtata tatgagtaaa cttggtctga cagttaccaa   2460
tgcttaatca gtgaggcacc tatctcagcg atctgtctat ttcgttcatc catagttgcc   2520
tgactccccg tggtgtagat aactacgata cgggagggct taccatctgg ccccagtgct   2580
gcaatgatac cgcgagaccc acgctcaccg gctccagatt tatcagcaat aaaccagcca   2640
gccgaagggc cgagcgcag  aagtggtcct gcaactttat ccgcctccat ccagtctatt   2700
aattgttgcc gggaagctag agtaagtagt tcgccagtta atagtttgcg caacgtggtt   2760
gccattgcta caggcatcgt ggtgtcacgc tcgtcgtttg gtatggcttc attcagctcc   2820
ggttcccaac gatcaaggcg agttacatga tcccccatgt tgtgcaaaaa agcggttagc   2880
tccttcggtc ctccgatcgt tgtcagaagt aagttggccg cagtgttatc actcatggtt   2940
atggcagcac tgcataattc tcttactgtc atgccatccg taagatgctt ttctgtgact   3000
ggtgagtact caaccaagtc attctgagaa tagtgtatgc ggcgaccgag ttgctcttgc   3060
ccggcgtcaa tacgggataa taccgcgcca catagcagaa ctttaaaagt gctcatcatt   3120
```

```
ggaaagcgtt cttcggggcg aaaactctca aggatcttac cgctgttgag atccagttcg    3180
atgtaaccca ctcgtgcacc caactgatct tcagcatctt ttactttcac cagcgtttct    3240
gggtgagcaa aaacaggaag gcaaaatgcc gcaaaaaagg gaataagggc gacacggaaa    3300
tgttgaatac tcatactctt ccttttttcaa tattattgaa gcatttatca gggttattgt    3360
ctcatgcgcg gatacatatt tgaatgtatt tagaaaaata aacaaatagg ggttccgcgc    3420
acatttcccc gaaaagtgcc acctgacgtc gc                                  3452
```

<210> SEQ ID NO 2
<211> LENGTH: 792
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: modified_base
<222> LOCATION: (86)..(185)
<223> OTHER INFORMATION: a, c, g, t, unknown or other
<220> FEATURE:
<221> NAME/KEY: modified_base
<222> LOCATION: (208)..(307)
<223> OTHER INFORMATION: a, c, g, t, unknown or other
<220> FEATURE:
<221> NAME/KEY: modified_base
<222> LOCATION: (330)..(429)
<223> OTHER INFORMATION: a, c, g, t, unknown or other
<220> FEATURE:
<221> NAME/KEY: modified_base
<222> LOCATION: (451)..(550)
<223> OTHER INFORMATION: a, c, g, t, unknown or other
<220> FEATURE:
<221> NAME/KEY: modified_base
<222> LOCATION: (593)..(692)
<223> OTHER INFORMATION: a, c, g, t, unknown or other

<400> SEQUENCE: 2

```
gagagagaga cgtcgctgag caggccctgt aatacgactc actatagggg gcgccggagc     60
ttagggataa cagggtaatg gtaccnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnncctag ggcgatcgcc gccggcgnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnntta attaaggcgc gccacgcgtn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnt acgtagcggc cgcgtcgacg nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn atttaaatcg gtccgcgtac gcatatagct aacagcctcg agnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nngctagcat taccctgtta tccctagccg    720
ctggcgcttc cctttagtga gggttaattt ccggagttta acgctcttc cgcttccttc    780 atgagagaga ga                                                       792
```

<210> SEQ ID NO 3
<211> LENGTH: 3452
<212> TYPE: DNA
<213> ORGANISM: Artificial Sequence
<220> FEATURE:
<223> OTHER INFORMATION: Description of Artificial Sequence: Synthetic

```
        plasmid
<220> FEATURE:
<221> NAME/KEY: modified_base
<222> LOCATION: (98)..(347)
<223> OTHER INFORMATION: a, c, g, t, unknown or other
<220> FEATURE:
<221> NAME/KEY: modified_base
<222> LOCATION: (411)..(430)
<223> OTHER INFORMATION: a, c, g, t, unknown or other
<220> FEATURE:
<221> NAME/KEY: modified_base
<222> LOCATION: (530)..(779)
<223> OTHER INFORMATION: a, c, g, t, unknown or other
<220> FEATURE:
<221> NAME/KEY: modified_base
<222> LOCATION: (810)..(1059)
<223> OTHER INFORMATION: a, c, g, t, unknown or other
<220> FEATURE:
<221> NAME/KEY: modified_base
<222> LOCATION: (1163)..(1182)
<223> OTHER INFORMATION: a, c, g, t, unknown or other
<220> FEATURE:
<221> NAME/KEY: modified_base
<222> LOCATION: (1240)..(1489)
<223> OTHER INFORMATION: a, c, g, t, unknown or other

<400> SEQUENCE: 3
tgagcagcgg ataacaattt cacacaggaa acagctatga ccatgattac tctgtagcat     60
ctatgtcggg tgcggagaaa gaggtaatga aatggcannn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnntgc catttcatta    360 cctctttctc cgcacccgac atagataggc cctgcgccgg cggcgatcgc nnnnnnnnnn    420
nnnnnnnnnn ttaattaaac gcgtggcgcg cctaactata acggtcctaa ggtagcgagg    480
taccgctggc cctagggtaa tacgactcac tatagggcca cataagtggn nnnnnnnnn    540 nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnc    780
cacttatgtg gtagggataa cagggtaatn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnna ttaccctgtt atccctatcc   1080
ctttagtgag ggttaattct cgaggcagga gctagctcgc taccttagga ccgttatagt   1140
tatacgtagt cgacgcggcc gcnnnnnnnn nnnnnnnnnn nncggtccga tttaaatcgt   1200
acgtccggat ggcaaacagc tattatgggt attatgggtn nnnnnnnnnn nnnnnnnnnn   1260
nnnnnnnnnn nnnnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnna cccataatac   1500
ccataatagc tgtttgccag ctacagagtt tactggccgt cgttttacaa cgtcgtgact   1560
```

```
gggaaaaccc tggcggttta aacgctcttc cgcttccttc atgtgagcaa aaggccagca   1620
aaaggccagg aaccgtaaaa aggccgcgtt gctggcgttt ttccataggc tccgcccccc   1680
tgacgagcat cacaaaaatc gacgctcaag tcagaggtgg cgaaacccga caggactata   1740
aagataccag gcgtttcccc ctggaagctc cctcgtgcgc tctcctgttc cgaccctgcc   1800
gcttaccgga tacctgtccg cctttctccc ttcgggaagc gtggcgcttt ctcatagctc   1860
acgctgtagg tatctcagtt cggtgtaggt cgttcgctcc aagctgggct gtgtgcacga   1920
accccccgtt cagcccgacc gctgcgcctt atccggtaac tatcgtcttg agtccaaccc   1980
ggtaagacac gacttatcgc cactggcagc agccactggt aacaggatta gcagagcgag   2040
gtatgtaggc ggtgctacag agttcttgaa gtggtggcct aactacggct acactagaag   2100
gacagtattt ggtatctgcg ctctgctgaa gccagttacc ttcggaaaaa gagttggtag   2160
ctcttgatcc ggcaaacaaa ccaccgctgg tagcggtggt ttttttgttt gcaagcagca   2220
gattacgcgc agaaaaaaag gatctcaaga agatcctttg atcttttcta cggggtctga   2280
cgctcagtgg aacgaaaact cacgttaagg gattttggtc atgataacta tgactctctt   2340
aaggtagcca aattcatgag attatcaaaa aggatcttca cctagatcct tttaaattaa   2400
aaatgaagtt ttaaatcaat ctaaagtata tatgagtaaa cttggtctga cagttaccaa   2460
tgcttaatca gtgaggcacc tatctcagcg atctgtctat ttcgttcatc catagttgcc   2520 tgactcccccg tggtgtagat aactacgata cgggagggct taccatctgg ccccagtgct   2580
gcaatgatac cgcgagaccc acgctcaccg gctccagatt tatcagcaat aaaccagcca   2640
gccggaaggg ccgagcgcag aagtggtcct gcaactttat ccgcctccat ccagtctatt   2700
aattgttgcc gggaagctag agtaagtagt tcgccagtta atagtttgcg caacgtggtt   2760
gccattgcta caggcatcgt ggtgtcacgc tcgtcgtttg gtatggcttc attcagctcc   2820
ggttcccaac gatcaaggcg agttacatga tcccccatgt tgtgcaaaaa agcggttagc   2880
tccttcggtc ctccgatcgt tgtcagaagt aagttggccg cagtgttatc actcatggtt   2940
atggcagcac tgcataattc tcttactgtc atgccatccg taagatgctt ttctgtgact   3000
ggtgagtact caaccaagtc attctgagaa tagtgtatgc ggcgaccgag ttgctcttgc   3060
ccggcgtcaa tacgggataa taccgcgcca catagcagaa ctttaaaagt gctcatcatt   3120
ggaaagcgtt cttcggggcg aaaactctca aggatcttac cgctgttgag atccagttcg   3180
atgtaaccca ctcgtgcacc caactgatct tcagcatctt ttactttcac cagcgtttct   3240
gggtgagcaa aaacaggaag gcaaaatgcc gcaaaaaagg aataagggc gacacggaaa   3300 tgttgaatac tcatactctt cctttttcaa tattattgaa gcatttatca gggttattgt   3360
ctcatgcgcg gatacatatt tgaatgtatt tagaaaaata acaaataggg gttccgcgc   3420 acatttcccc gaaaagtgcc acctgacgtc gc                                3452
```

<210> SEQ ID NO 4
<211> LENGTH: 1628
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: modified_base
<222> LOCATION: (114)..(363)
<223> OTHER INFORMATION: a, c, g, t, unknown or other
<220> FEATURE:
<221> NAME/KEY: modified_base

```
<222> LOCATION: (427)..(446)
<223> OTHER INFORMATION: a, c, g, t, unknown or other
<220> FEATURE:
<221> NAME/KEY: modified_base
<222> LOCATION: (546)..(795)
<223> OTHER INFORMATION: a, c, g, t, unknown or other
<220> FEATURE:
<221> NAME/KEY: modified_base
<222> LOCATION: (826)..(1075)
<223> OTHER INFORMATION: a, c, g, t, unknown or other
<220> FEATURE:
<221> NAME/KEY: modified_base
<222> LOCATION: (1179)..(1198)
<223> OTHER INFORMATION: a, c, g, t, unknown or other
<220> FEATURE:
<221> NAME/KEY: modified_base
<222> LOCATION: (1256)..(1505)
<223> OTHER INFORMATION: a, c, g, t, unknown or other

<400> SEQUENCE: 4
gagagagaga cgtcgctgag cagcggataa caatttcaca caggaaacag ctatgaccat      60
gattactctg tagcatctat gtcgggtgcg gagaaagagg taatgaaatg gcannnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnntgccatt tcattacctc tttctccgca cccgacatag ataggccctg cgccggcggc     420
gatcgcnnnn nnnnnnnnnn nnnnnnttaa ttaaacgcgt ggcgcgccta actataacgg     480
tcctaaggta gcgaggtacc gctggcccta gggtaatacg actcactata gggccacata     540
agtggnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnccact tatgtggtag ggataacagg gtaatnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnattac    1080
cctgttatcc ctatccctt agtgagggtt aattctcgag gcaggagcta gctcgctacc    1140
ttaggaccgt tatagttata cgtagtcgac gcggccgcnn nnnnnnnnnn nnnnnnnncg    1200
gtccgattta atcgtacgt ccggatggca aacagctatt atgggtatta tgggtnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnaccca taatacccat aatagctgtt tgccagctac agagtttact ggccgtcgtt    1560
ttacaacgtc gtgactggga aaaccctggc ggtttaaacg ctcttccgct tccttcatga    1620
gagagaga                                                             1628

<210> SEQ ID NO 5
```

<211> LENGTH: 2092
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 5

| | | | | | |
|---|---|---|---|---|---|
| tgagcgtaat | acgactcact | atagggaggc | cctgcgatcg | ccgccggcgg | atatcggagc | 60 |
| tgctgggccc | agggagcttc | tagaggagct | ggatccgctg | gagaattcgg | agctggaaag | 120 |
| cttggagctg | ctctgcaggg | agctgcatgc | gctggcgcac | agctgttaat | taaggcgcgc | 180 |
| cacgcgttcc | ggattcccctt | tagtgagggt | taattgttta | aacgctcttc | cgcttccttc | 240 |
| atgtgagcaa | aaggccagca | aaaggccagg | aaccgtaaaa | aggccgcgtt | gctggcgttt | 300 |
| ttccataggc | tccgccccc | tgacgagcat | cacaaaaatc | gacgctcaag | tcagaggtgg | 360 |
| cgaaacccga | caggactata | aagataccag | gcgtttcccc | ctggaagctc | cctcgtgcgc | 420 |
| tctcctgttc | cgaccctgcc | gcttaccgga | tacctgtccg | cctttctccc | ttcgggaagc | 480 |
| gtggcgcttt | ctcatagctc | acgctgtagg | tatctcagtt | cggtgtaggt | cgttcgctcc | 540 |
| aagctgggct | gtgtgcacga | accccccgtt | cagcccgacc | gctgcgcctt | atccggtaac | 600 |
| tatcgtcttg | agtccaaccc | ggtaagacac | gacttatcgc | cactggcagc | agccactggt | 660 |
| aacaggatta | gcagagcgag | gtatgtaggc | ggtgctacag | agttcttgaa | gtggtggcct | 720 |
| aactacggct | acactagaag | gacagtattt | ggtatctgcg | ctctgctgaa | gccagttacc | 780 |
| ttcggaaaaa | gagttggtag | ctcttgatcc | ggcaaacaaa | ccaccgctgg | tagcggtggt | 840 |
| ttttttgttt | gcaagcagca | gattacgcgc | agaaaaaaag | gatctcaaga | agatcctttg | 900 |
| atcttttcta | cggggtctga | cgctcagtgg | aacgaaaact | cacgttaagg | gattttggtc | 960 |
| atgataacta | tgactctctt | aaggtagcca | aattcatgag | attatcaaaa | aggatcttca | 1020 |
| cctagatcct | tttaaattaa | aaatgaagtt | ttaaatcaat | ctaaagtata | tatgagtaaa | 1080 |
| cttggtctga | cagttaccaa | tgcttaatca | gtgaggcacc | tatctcagcg | atctgtctat | 1140 |
| ttcgttcatc | catagttgcc | tgactccccg | tggtgtagat | aactacgata | cgggagggct | 1200 |
| taccatctgg | ccccagtgct | gcaatgatac | cgcgagaccc | acgctcaccg | gctccagatt | 1260 |
| tatcagcaat | aaaccagcca | gccggaaggg | ccgagcgcag | aagtggtcct | gcaactttat | 1320 |
| ccgcctccat | ccagtctatt | aattgttgcc | gggaagctag | agtaagtagt | tcgccagtta | 1380 |
| atagtttgcg | caacgtggtt | gccattgcta | caggcatcgt | ggtgtcacgc | tcgtcgtttg | 1440 |
| gtatggcttc | attcagctcc | ggttcccaac | gatcaaggcg | agttacatga | tcccccatgt | 1500 |
| tgtgcaaaaa | agcggttagc | tccttcggtc | ctccgatcgt | tgtcagaagt | aagttggccg | 1560 |
| cagtgttatc | actcatggtt | atggcagcac | tgcataattc | tcttactgtc | atgccatccg | 1620 |
| taagatgctt | ttctgtgact | ggtgagtact | caaccaagtc | attctgagaa | tagtgtatgc | 1680 |
| ggcgaccgag | ttgctcttgc | ccggcgtcaa | tacgggataa | taccgcgcca | catagcagaa | 1740 |
| ctttaaaagt | gctcatcatt | ggaaagcgtt | cttcggggcg | aaaactctca | aggatcttac | 1800 |
| cgctgttgag | atccagttcg | atgtaaccca | ctcgtgcacc | caactgatct | tcagcatctt | 1860 |
| ttactttcac | cagcgtttct | gggtgagcaa | aaacaggaag | gcaaaatgcc | gcaaaaaagg | 1920 |
| gaataagggc | gacacggaaa | tgttgaatac | tcatactctt | cctttttcaa | tattattgaa | 1980 |
| gcatttatca | gggttattgt | ctcatgcgcg | gatacatatt | tgaatgtatt | tagaaaaata | 2040 |
| aacaaatagg | ggttccgcgc | acatttcccc | gaaaagtgcc | acctgacgtc | gc | 2092 |

<210> SEQ ID NO 6
<211> LENGTH: 234
<212> TYPE: DNA
<213> ORGANISM: Artificial Sequence
<220> FEATURE:
<223> OTHER INFORMATION: Description of Artificial Sequence: Synthetic
     plasmid

<400> SEQUENCE: 6

| cgctgagcgt | aatacgactc | actataggga | ggccctgcga | tcgccgccgg | cggatatcgg | 60 |
| agctgctggg | cccagggagc | ttctagagga | gctggatccg | ctggagaatt | cggagctgga | 120 |
| aagcttggag | ctgctctgca | gggagctgca | tgcgctggcg | cacagctgtt | aattaaggcg | 180 |
| cgccacgcgt | tccggattcc | ctttagtgag | ggttaattgt | ttaaacgctc | ttcc | 234 |

<210> SEQ ID NO 7
<211> LENGTH: 2097
<212> TYPE: DNA
<213> ORGANISM: Artificial Sequence
<220> FEATURE:
<223> OTHER INFORMATION: Description of Artificial Sequence: Synthetic
     plasmid

<400> SEQUENCE: 7

| tgagcgtaat | acgactcact | atagggaggc | cctgttaatt | aaggcgcgcc | acgcgtgata | 60 |
| tcggagctgc | tgggcccagg | gagcttctag | aggagctgga | tccgctggag | aattcggagc | 120 |
| tggaaagctt | ggagctgctc | tgcagggagc | tgcatgcgct | ggcgcacagc | tgtacgtagc | 180 |
| ggccgcgtcg | actccggatt | cccttcagtg | agggttaatt | gtttaaacgc | tcttccgctt | 240 |
| ccttcatgtg | agcaaaaggc | cagcaaaagg | ccaggaaccg | taaaaaggcc | gcgttgctgg | 300 |
| cgttttccca | taggctccgc | cccctgacg | agcatcacaa | aaatcgacgc | tcaagtcaga | 360 |
| ggtggcgaaa | cccgacagga | ctataaagat | accaggcgtt | tccccctgga | agctccctcg | 420 |
| tgcgctctcc | tgttccgacc | ctgccgctta | ccggatacct | gtccgccttt | ctcccttcgg | 480 |
| gaagcgtggc | gctttctcat | agctcacgct | gtaggtatct | cagttcggtg | taggtcgttc | 540 |
| gctccaagct | gggctgtgtg | cacgaacccc | ccgttcagcc | cgaccgctgc | gccttatccg | 600 |
| gtaactatcg | tcttgagtcc | aacccggtaa | gacacgactt | atcgccactg | gcagcagcca | 660 |
| ctggtaacag | gattagcaga | gcgaggtatg | taggcggtgc | tacagagttc | ttgaagtggt | 720 |
| ggcctaacta | cggctacact | agaaggacag | tatttggtat | ctgcgctctg | ctgaagccag | 780 |
| ttaccttcgg | aaaaagagtt | ggtagctctt | gatccggcaa | acaaaccacc | gctggtagcg | 840 |
| gtggtttttt | tgtttgcaag | cagcagatta | cgcgcagaaa | aaaaggatct | caagaagatc | 900 |
| ctttgatctt | ttctacgggg | tctgacgctc | agtggaacga | aaactcacgt | taagggattt | 960 |
| tggtcatgat | aactatgact | ctcttaaggt | agccaaattc | atgagattat | caaaaaggat | 1020 |
| cttcacctag | atcctttaa | attaaaaatg | aagttttaaa | tcaatctaaa | gtatatatga | 1080 |
| gtaaacttgg | tctgacagtt | accaatgctt | aatcagtgag | gcacctatct | cagcgatctg | 1140 |
| tctatttcgt | tcatccatag | ttgcctgact | ccccgtggtg | tagataacta | cgatacggga | 1200 |
| gggcttacca | tctggcccca | gtgctgcaat | gataccgcga | gacccacgct | caccggctcc | 1260 |
| agatttatca | gcaataaacc | agccagccgg | aagggccgag | cgcagaagtg | gtcctgcaac | 1320 |
| tttatccgcc | tccatccagt | ctattaattg | ttgccgggaa | gctagagtaa | gtagttcgcc | 1380 |
| agttaatagt | ttgcgcaacg | tggttgccat | tgctacaggc | atcgtggtgt | cacgctcgtc | 1440 |
| gtttggtatg | gcttcattca | gctccggttc | ccaacgatca | aggcgagtta | catgatcccc | 1500 |

```
catgttgtgc aaaaaagcgg ttagctcctt cggtcctccg atcgttgtca gaagtaagtt    1560
ggccgcagtg ttatcactca tggttatggc agcactgcat aattctctta ctgtcatgcc    1620
atccgtaaga tgcttttctg tgactggtga gtactcaacc aagtcattct gagaatagtg    1680
tatgcggcga ccgagttgct cttgcccggc gtcaatacgg ataataccg cgccacatag     1740 cagaacttta aaagtgctca tcattggaaa gcgttcttcg gggcgaaaac tctcaaggat    1800
cttaccgctg ttgagatcca gttcgatgta acccactcgt gcacccaact gatcttcagc    1860
atcttttact ttcaccagcg tttctgggtg agcaaaaaca ggaaggcaaa atgccgcaaa    1920
aaagggaata agggcgacac ggaaatgttg aatactcata ctcttccttt ttcaatatta    1980
ttgaagcatt tatcagggtt attgtctcat gcgcggatac atatttgaat gtatttagaa    2040
aaataaacaa atagggttc cgcgcacatt tccccgaaaa gtgccacctg acgtcgc         2097
```

<210> SEQ ID NO 8
<211> LENGTH: 239
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 8

```
cgctgagcgt aatacgactc actataggga ggccctgtta attaaggcgc gccacgcgtg      60
atatcggagc tgctgggccc agggagcttc tagaggagct ggatccgctg gagaattcgg     120
agctggaaag cttggagctg ctctgcaggg agctgcatgc gctggcgcac agctgtacgt     180
agcggccgcg tcgactccgg attccctta gtgagggtta ttgtttaaa cgctcttcc       239
```

<210> SEQ ID NO 9
<211> LENGTH: 2096
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 9

```
tgagcgtaat acgactcact atagggaggc cctgtacgta gcggccgcgt cgacgatatc      60
ggagctgctg ggcccaggga gcttctagag gagctggatc cgctggagaa ttcggagctg     120
gaaagcttgg agctgctctg cagggagctg catgcgctgg cgcacagctg atttaaatcg     180
gtccgcgtac gtccggattc cctttagtga gggttaattg tttaaacgct cttccgcttc     240
cttcatgtga gcaaaaggcc agcaaaaggc caggaaccgt aaaaaggccg cgttgctggc     300 gttttccat aggctccgcc cccctgacga gcatcacaaa aatcgacgct caagtcagag      360
gtggcgaaac ccgacaggac tataaagata ccaggcgttt ccccctggaa gctccctcgt     420
gcgctctcct gttccgaccc tgccgcttac cggatacctg tccgcctttc tcccttcggg     480
aagcgtggcg ctttctcata gctcacgctg taggtatctc agttcggtgt aggtcgttcg     540
ctccaagctg ggctgtgtgc acgaaccccc cgttcagccc gaccgctgcg ccttatccgg     600
taactatcgt cttgagtcca acccggtaag acacgactta tcgccactgg cagcagccac    660
tggtaacagg attagcagag cgaggtatgt aggcggtgct acagagttct tgaagtggtg     720
gcctaactac ggctacacta aggacagt atttggtatc tgcgctctgc tgaagccagt      780
taccttcgga aaaagagttg gtagctcttg atccggcaaa caaaccaccg ctggtagcgg     840
```

```
tggttttttt gtttgcaagc agcagattac gcgcagaaaa aaaggatctc aagaagatcc      900
tttgatcttt tctacggggt ctgacgctca gtggaacgaa aactcacgtt aagggatttt      960
ggtcatgata actatgactc tcttaaggta gccaaattca tgagattatc aaaaaggatc     1020
ttcacctaga tccttttaaa ttaaaaatga agttttaaat caatctaaag tatatatgag     1080
taaacttggt ctgacagtta ccaatgctta atcagtgagg cacctatctc agcgatctgt     1140
ctatttcgtt catccatagt tgcctgactc cccgtggtgt agataactac gatacgggag     1200
ggcttaccat ctggcccag tgctgcaatg ataccgcgag acccacgctc accggctcca     1260
gatttatcag caataaacca gccagccgga agggccgagc gcagaagtgg tcctgcaact     1320
ttatccgcct ccatccagtc tattaattgt tgccgggaag ctagagtaag tagttcgcca     1380
gttaatagtt tgcgcaacgt ggttgccatt gctacaggca tcgtggtgtc acgctcgtcg     1440
tttggtatgg cttcattcag ctccggttcc caacgatcaa ggcgagttac atgatccccc     1500
atgttgtgca aaaaagcggt tagctccttc ggtcctccga tcgttgtcag aagtaagttg     1560
gccgcagtgt tatcactcat ggttatggca gcactgcata attctcttac tgtcatgcca     1620
tccgtaagat gcttttctgt gactggtgag tactcaacca agtcattctg agaatagtgt     1680
atgcggcgac cgagttgctc ttgcccggcg tcaatacggg ataataccgc gccacatagc     1740
agaactttaa aagtgctcat cattggaaag cgttcttcgg ggcgaaaact ctcaaggatc     1800
ttaccgctgt tgagatccag ttcgatgtaa cccactcgtg cacccaactg atcttcagca     1860
tcttttactt tcaccagcgt ttctgggtga gcaaaaacag gaaggcaaaa tgccgcaaaa     1920
aagggaataa gggcgacacg gaaatgttga atactcatac tcttcctttt tcaatattat     1980
tgaagcattt atcagggtta ttgtctcatg cgcggataca tatttgaatg tatttagaaa     2040
aataaacaaa taggggttcc gcgcacattt ccccgaaaag tgccacctga cgtcgc        2096

<210> SEQ ID NO 10
<211> LENGTH: 238
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 10
cgctgagcgt aatacgactc actataggga ggccctgtac gtagcggccg cgtcgacgat       60
atcggagctg ctgggcccag ggagcttcta gaggagctgg atccgctgga gaattcggag      120
ctggaaagct tggagctgct ctgcagggag ctgcatgcgc tggcgcacag ctgatttaaa      180
tcggtccgcg tacgtccgga ttcccttttag tgagggttaa ttgtttaaac gctcttcc      238

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tagggataac agggtaat                                                      18

<210> SEQ ID NO 12
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 12
attaccctgt tatccta                                                        18

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tagggataac ccta                                                           14

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other

<400> SEQUENCE: 14
ccannnnnnt gg                                                             12

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccagataaca gggtaatatt accctgttat gtgg                                     34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccacataaca gggtaatatt accctgttat ctgg                                     34

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 17
```

```
gacnnnnngt c                                                                11
```

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 18

```
cacnnnnngt c                                                                11
```